(12) United States Patent
Edwards et al.

(10) Patent No.: US 9,681,914 B2
(45) Date of Patent: *Jun. 20, 2017

(54) APPARATUS AND METHOD FOR TUBESET WITH DRIVE AXLE

(71) Applicant: Gyrus ACMI, Inc., Southborough, MA (US)

(72) Inventors: Kevin C. Edwards, Olive Branch, MS (US); Jay A. Casey, Memphis, TN (US); Peter Y. Wong, Arlington, TN (US); Allen C. Palmer, Arlington, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/542,798

(22) Filed: Nov. 17, 2014

(65) Prior Publication Data

US 2015/0133922 A1 May 14, 2015

Related U.S. Application Data

(63) Continuation of application No. 13/804,308, filed on Mar. 14, 2013, now Pat. No. 8,920,419.

(Continued)

(51) Int. Cl.
*A61B 18/14* (2006.01)
*A61B 17/32* (2006.01)
(Continued)

(52) U.S. Cl.
CPC ...... *A61B 18/149* (2013.01); *A61B 17/32002* (2013.01); *A61B 17/320016* (2013.01);
(Continued)

(58) Field of Classification Search
CPC .. A61B 2018/00916; A61B 2018/0091; A61B 2018/00982; A61B 2034/2055–2034/2057
See application file for complete search history.

(56) References Cited

U.S. PATENT DOCUMENTS 3,955,284 A 5/1976 Balson
4,878,493 A 11/1989 Pasternak et al.
(Continued)

FOREIGN PATENT DOCUMENTS

EP 2510891 A1 10/2012

OTHER PUBLICATIONS

Gyrus ACMI; Handpiece Cleaning and Maintenance Jun. 1, 2006.
(Continued)

*Primary Examiner* — Michael Kahelin
(74) *Attorney, Agent, or Firm* — The Dobrusin Law Firm, P.C.; Daniel P. Aleksynas

(57) ABSTRACT

A device comprising: a handpiece having one or more attachment ports; a tubeset having one or more attachment features for connecting the tubeset to the one or more attachment ports in the handpiece; a removable tip having an attachment arm for attaching to the one or more attachment ports in the handpiece; wherein the device comprises one or more of the following: the handpiece includes an attachment port that attaches the handpiece to an active lead and a return lead and the device is adapted to use only the active lead or both leads so that the device can switch between bi-polar energy and mono-polar energy; the tubeset has one or more fluid conduits that are in fluid communication with the removable tip, wherein the removable tip is located at a distal end of the device; and the handpiece connects to one or more electrical input lines; the tubeset connects to one or (Continued)

more fluid lines, and the removable tip is free of direct connection to both the one or more electrical input lines and the one or more fluid lines.

20 Claims, 9 Drawing Sheets

Related U.S. Application Data

(60) Provisional application No. 61/769,480, filed on Feb. 26, 2013, provisional application No. 61/731,919, filed on Nov. 30, 2012.

(51) Int. Cl.
 A61B 18/12 (2006.01)
 A61B 18/00 (2006.01)
 A61B 17/00 (2006.01)

(52) U.S. Cl.
 CPC .......... *A61B 18/1206* (2013.01); *A61B 18/14* (2013.01); *A61B 18/1402* (2013.01); *A61B 18/1482* (2013.01); *A61B 2017/0046* (2013.01); *A61B 2017/00225* (2013.01); *A61B 2017/00464* (2013.01); *A61B 2017/00473* (2013.01); *A61B 2017/00482* (2013.01); *A61B 2017/00526* (2013.01); *A61B 2018/0019* (2013.01); *A61B 2018/0094* (2013.01); *A61B 2018/00178* (2013.01); *A61B 2018/00208* (2013.01); *A61B 2018/00708* (2013.01); *A61B 2018/126* (2013.01); *A61B 2018/1253* (2013.01); *Y10T 29/49002* (2015.01); *Y10T 29/49169* (2015.01)

(56) References Cited

U.S. PATENT DOCUMENTS

| | | | |
|---|---|---|---|
| 5,230,704 A | 7/1993 | Moberg et al. | |
| 5,275,609 A | 1/1994 | Pingleton et al. | |
| 5,352,222 A | 10/1994 | Rydell et al. | |
| 5,395,312 A | 3/1995 | Desai | |
| 5,405,348 A | 4/1995 | Anspach et al. | |
| 5,413,556 A | 5/1995 | Whittingham | |
| 5,492,527 A | 2/1996 | Glowa et al. | |
| 5,560,373 A | 10/1996 | De Santis | |
| 5,569,254 A | 10/1996 | Carlson et al. | |
| 5,609,573 A | 3/1997 | Sandock | |
| 5,620,415 A | 4/1997 | Lucey et al. | |
| 5,712,543 A | 1/1998 | Sjostrom | |
| 5,792,167 A | 8/1998 | Kablik et al. | |
| 5,810,809 A | 9/1998 | Rydell et al. | |
| 5,814,044 A | 9/1998 | Hooven | |
| 5,849,023 A | 12/1998 | Mericle | |
| 5,873,886 A | 2/1999 | Larsen et al. | |
| 5,899,915 A | 5/1999 | Saadat | |
| 5,904,681 A | 5/1999 | West, Jr. | |
| 6,042,593 A | 3/2000 | Storz et al. | |
| 6,053,923 A | 4/2000 | Veca et al. | |
| 6,059,719 A * | 5/2000 | Yamamoto | A61B 1/00059 600/104 |
| 6,074,386 A | 6/2000 | Goble et al. | |
| 6,120,462 A * | 9/2000 | Hibner | A61B 10/0275 600/566 |
| 6,221,088 B1 | 4/2001 | Bays | |
| 6,246,638 B1 | 6/2001 | Zook et al. | |
| 6,293,957 B1 | 9/2001 | Peters et al. | |
| 6,296,638 B1 | 10/2001 | Davison et al. | |
| 6,716,215 B1 | 4/2004 | David et al. | |
| 6,752,816 B2 | 6/2004 | Culp et al. | |
| 6,824,550 B1 | 11/2004 | Noriega | |
| 6,979,332 B2 | 12/2005 | Adams | |
| 7,179,255 B2 | 2/2007 | Lettice et al. | |
| 7,237,990 B2 | 7/2007 | Deng | |
| 7,416,539 B2 | 8/2008 | Johnston et al. | |
| 7,442,191 B2 | 10/2008 | Hovda et al. | |
| 7,674,263 B2 | 3/2010 | Ryan | |
| 8,920,419 B2 | 12/2014 | Edwards et al. | |
| 9,113,897 B2 * | 8/2015 | Deborski | A61B 18/14 |
| 2001/0047183 A1 | 11/2001 | Privitera et al. | |
| 2002/0165549 A1 | 11/2002 | Owusu-Akyaw et al. | |
| 2003/0097129 A1 | 5/2003 | Davison et al. | |
| 2005/0096671 A1 | 5/2005 | Wellman et al. | |
| 2005/0222566 A1 | 10/2005 | Nakahira | |
| 2009/0270896 A1 | 10/2009 | Sullivan et al. | |
| 2010/0094315 A1 | 4/2010 | Beardsley et al. | |
| 2010/0317998 A1 | 12/2010 | Hibner et al. | |
| 2011/0009856 A1 | 1/2011 | Jorgensen et al. | |
| 2011/0066142 A1 | 3/2011 | Tal | |
| 2011/0301578 A1 | 12/2011 | Muniz-Medina et al. | |
| 2012/0241499 A1 | 9/2012 | Baxter et al. | |
| 2013/0004595 A1 | 1/2013 | Bhatia | |
| 2013/0085498 A1 | 4/2013 | Matusaitis et al. | |
| 2013/0291386 A1 | 11/2013 | Gambino et al. | |
| 2014/0155888 A1 | 6/2014 | Edwards et al. | |
| 2015/0073405 A1 | 3/2015 | Edwards et al. | |

OTHER PUBLICATIONS

International Search Report and Written Opinion dated Dec. 12, 2013 for International Application No. PCT/US2013/065830.
PKS Cutting Forceps, General Surgery Products, Gyrus ACMI, An Olympus Company, available at www.gyrusacmi,com/user/display.cfm?display=product&pid=9063&catud=69&mainacat=Gene.
Potentially Related Patent Application, U.S. Appl. No. 13/769,416, filed Mar. 12, 2013.
Potentially Related Patent Application, U.S. Appl. No. 13/803,380, filed Mar. 14, 2013.
Potentially Related Patent Application, U.S. Appl. No. 13/826,892, filed Mar. 14, 2013.
Potentially Related Patent Application, U.S. Appl. No. 13/804,308 (Granted U.S. Pat. No. 8,920,419) filed Mar. 14, 2013.
Potentially Related Patent Application, U.S. Appl. No. 14/542,773 (Publication No. 2015/0073405) filed Nov. 11, 2014.
European Office Action for Application Serial No. 13786571.3-1659 (Ref. POA-2015-009) issued on Mar. 12, 2015.
European Office Action for Application No. 13786571.3-1659, issued May 30, 2016.

\* cited by examiner

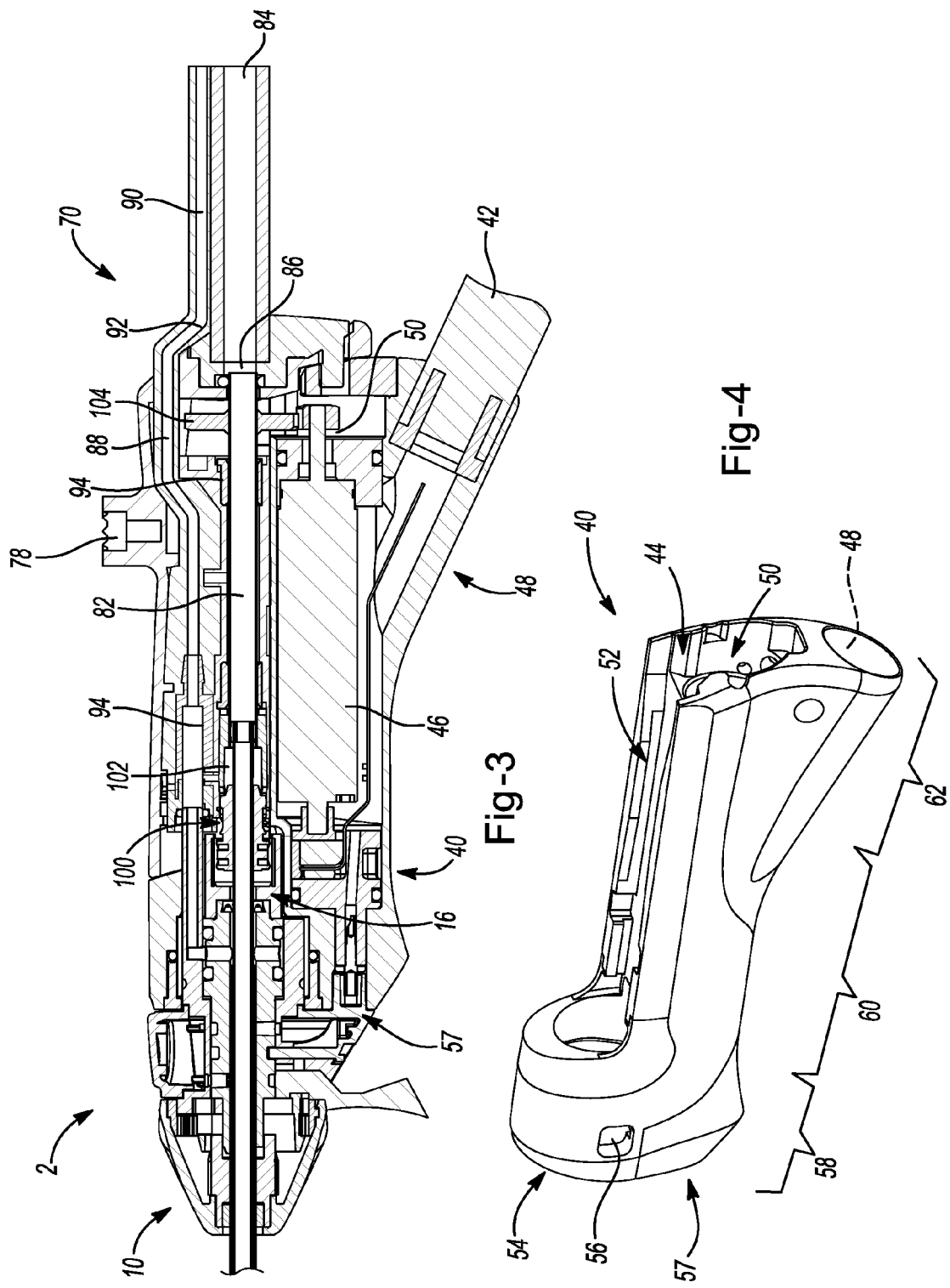

APPARATUS AND METHOD FOR TUBESET WITH DRIVE AXLE

FIELD

The present teachings generally relate to a debrider, and more specifically a microdebrider with interchangeable replaceable parts and a method of installing the parts.

BACKGROUND

Generally, most debriders are made of a single piece of surgical metal that can be sterilized repeatedly between surgeries. The single piece of metal includes multiple moving parts inside that may be made of different materials. The debrider after use is placed into a sterilization device such as an autoclave and rapidly heated, thereby, sterilizing the device. Due to the high temperatures used in the autoclave, to sterilize the debrider, the debrider either will rest for an extended period of time to cool, or the debrider can be placed in a cooling fluid such as water to cool the debrider. This rapid heating and then cooling causes the parts made of different materials to expand and contract at different rates which may cause the parts to prematurely wear, become misaligned, increase tolerances between parts, decrease tolerances between parts, or a combination thereof. Additionally, the rapid cycling of the debrider from hot to cold may cause the drive systems and/or drive components to be less reliable than a new debrider. Thus, what is needed is a debrider that can be rapidly sterilized between uses without causing premature failure and/or reliability issues with components of the debrider.

Currently, single piece debriders are only used with bipolar energy or no energy. This is due to the single piece assembly of the debriders causing a risk of shock for a user when the debrider is used with a monopolar energy source. Thus, to eliminate the risk of shock debriders are not available with monopolor energy.

Additionally, most debriders include interchangeable tips that are added and removed from the debrider depending on the particular need for a particular procedure. The interchangeable tips are removed from sterile packaging and inserted into the single piece surgical instrument after the surgical instrument is sterilized. After a procedure is performed the interchangeable tip is removed and discarded while the debrider is sterilized. The componentry of the surgical instrument and the interchangeable tip need a high degree of alignment so that the tip does not slip or stop working during use. Additionally, if tolerances in the surgical instrument change it may become increasingly difficult to insert the interchangeable tip into the surgical instrument. Alternatively, if the tolerances become too large the surgical instrument may not adequately supply power to the interchangeable tip during a procedure and/or the surgical instrument may not adequately stabilize the interchangeable tip.

Examples of some known debriders and cutting instruments that are used may be found in U.S. Pat. Nos. 5,230,704; 5,560,373; 5,810,809; 6,053,923; 6,246,638; 6,716,215; 6,979,332; 7,179,255; and 7,442,191 all of which are incorporated by reference herein for all purposes. Examples of some known surgical devices including disposable parts may be found in U.S. Pat. Nos. 3,955,284; 5,230,704; 5,560,373; and 5,849,023 all of which are incorporated by reference herein for all purposes. It would be attractive to have a surgical instrument that is reusable without subjecting all of the moving parts to thermal cycling. It would be attractive to have a device that can use bipolar energy, monopolar energy, or no energy during surgery. It would be attractive to have a surgical instrument where the reusable portion is substantially free of contact with materials removed from a patient and/or added to a patient during surgery.

SUMMARY

The present teachings meet one or more of the present needs by providing: a device comprising: a handpiece having one or more attachment ports; a tubeset having one or more attachment features for connecting the tubeset to the one or more attachment ports in the handpiece; a removable tip having an attachment arm for attaching to the one or more attachment ports in the handpiece; wherein the device comprises one or more of the following: the handpiece includes an attachment port that attaches the handpiece to an active lead and a return lead and the device is adapted to use only the active lead or both leads so that the device can switch between bi-polar energy and mono-polar energy; the tubeset has one or more fluid conduits that are in fluid communication with the removable tip, wherein the removable tip is located at a distal end of the device; and the handpiece connects to one or more electrical input lines; the tubeset connects to one or more fluid lines, and the removable tip is free of direct connection to both the one or more electrical input lines and the one or more fluid lines.

Another possible embodiment of the present teachings comprises: a microdebrider comprising: a tubeset having: one or more attachment features, one or more couplers; and a drivetrain; a removable tip having an attachment arm; a handpiece including: a tip attachment port so that the removable tip is attached to the handpiece via the attachment arm; a tubeset attachment port so that the one or more attachment features of the tubeset align the tubeset with the handpiece and connect the tubeset and the handpiece together; and one or more of the following: the handpiece includes an attachment port that attaches the handpiece to an active lead and a return lead and the device is adapted to use only the active lead or both leads so that the device can switch between bi-polar energy and mono-polar energy; one or more fluid conduits in the tubeset that are in fluid communication with the removable tip, wherein the removable tip is located at a distal end of the device; and one or more electrical input lines in the handpiece; one or more fluid lines in the tubeset, and wherein the removable tip is free of direct connection to both the one or more electrical input lines and the one or more fluid lines.

One possible method for assembling the device taught here comprising (a) obtaining each individual part of the device of any of the preceding claims; (b) connecting a power source to the handpiece via a first attachment port of the one or more attachment ports; (c) connecting the removable tip to the hand piece via a second attachment port of the one or more attachment ports; and (d) connecting the tubeset to the handpiece via a third attachment port of the one or more attachment ports.

The teachings herein provide a surgical instrument that is reusable without subjecting all of the moving parts to thermal cycling. The device of the teachings herein can use both bipolar and monopolar energy during surgery. The surgical instrument taught herein includes a reusable portion which is substantially free of contact with materials removed from a patient and/or added to a patient during surgery.

BRIEF DESCRIPTION OF THE DRAWINGS

FIG. 3 illustrates a cross-sectional side view of one example of a microdebrider;

FIG. 4 illustrates a perspective view of one example of a handpiece;

DETAILED DESCRIPTION

Figure 1:
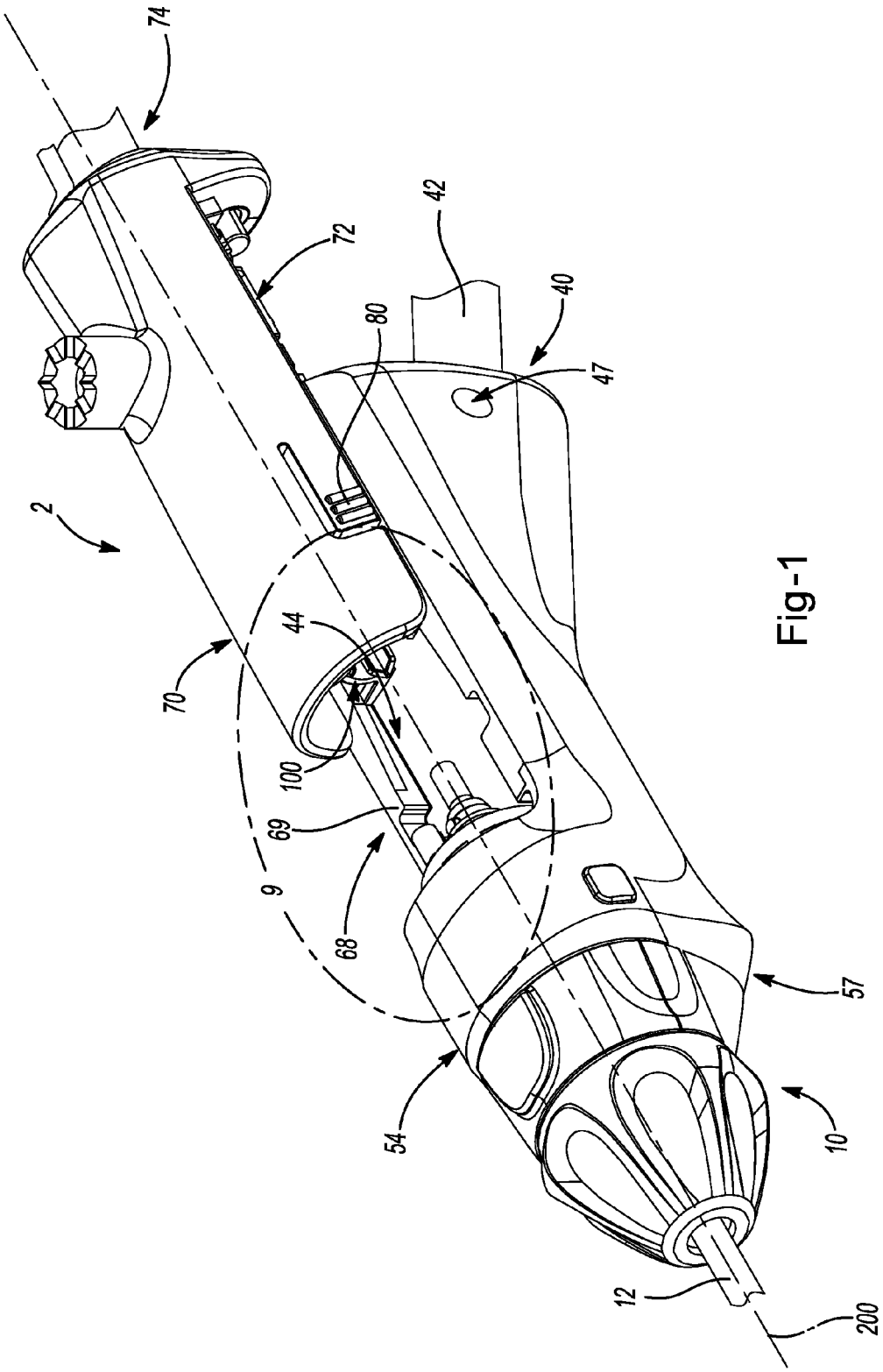
FIG. 1 illustrates a front perspective view of a tubeset being attached to a handpiece.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein describe a surgical instrument, preferably the surgical instrument is a debrider, and more preferably the surgical instrument is a microdebrider. As discussed herein the surgical instrument is referred to as a microdebrider. The microdebrider may be any microdebrider that may be used to perform a surgical procedure. Examples of surgical procedures that the microdebrider of the teachings herein may be used to perform are a tonsillectomy, turbinoplasty, septoplasty, supraglottoplasty, sinus surgery, throat surgery, small joint arthroscopy, large joint arthroscopy, spinal surgery, disc surgery, the like, or a combination thereof. The microdebrider as discussed herein includes an interchangeable tip, a handpiece, and a tubeset.

The interchangeable tip may include wiring so that the interchangeable tip may be used with a monopolar energy source, a bi-polar energy source, free of energy, or a combination thereof. The interchangeable tip may be configured so that based upon the arrangement of the wires within the tip, the tip applies a monopolar energy, and/or a bipolar energy to a procedure site. Alternatively, the interchangeable tip may be devoid of wiring for use with a mechanical tip, thereby the tip may not be configured to apply either monopolar or bipolar energy to a procedure site. The interchangeable tips including a monopolar energy attachment, a bipolar energy attachment, no energy attachment, or a combination thereof include one or more mechanical functionality. The interchangeable tips may include mechanical functionality including a stylet, one or more connecting tabs, a drive attachment, or a combination thereof so that the mechanical functionality may perform one or more of the procedures discussed herein. The interchangeable tip may include an enclosure that houses the circuitry. Other teachings regarding the blade circuitry, connectors, identification circuits, control circuits, connectors, or a combination thereof may be gleaned from the teachings herein, including those of Paragraph Nos.; 5-9 and 0024-0053 and Figure Nos. 1-7D and corresponding verbal description in paragraphs 0054-0064 of U.S. patent application Ser. No. 13/803,380, filed on Mar. 14, 2012, incorporated by reference herein for all purposes regarding the blade circuitry, connectors, identification circuits, control circuits, connectors, detection circuits, or a combination thereof.

The stylet may be any stylet that may be used to perform a surgical procedure. The stylet may be rigid, flexible, semi-flexible, include a flexible portion, or a combination thereof. The stylet may be one piece. Preferably, the stylet has an outer tube with an inner tube that rotates within the outer tube. The outer tube may be substantially stationary during use. The outer tube may be rotatable so that an opening in the tube may be angled to correspond to a site of interest. For example, during a procedure the user may rotate the outer tube and corresponding opening so that the opening aligns to the site of interest so that the user may work at the site of interest without having to adjust the device, remove the device and adjust the opening, or a combination thereof. A portion of the outer tube and/or corresponding feature may include an indicator showing the location of the opening in the outer tube so that the location of the opening is known without additional viewing equipment, removing the device from the site of interest, or both. The inner tube, the outer tube, or both may rotate clockwise, counterclockwise, or both. The inner tube may rotate and move back and forth during use. Preferably, the inner tube only rotates during use. The two or more tubes may be rotated relative to each other and the rotation of the tubes may be monitored by a sensor in the blade assembly, the handpiece, or both by two or more transmitters, magnets, an encapsulation connector, or a combination thereof located in the blade module (i.e., mechanical enclosure) of the blade assembly, the handpiece, or both. Other teachings regarding the encapsulation connector, the two or more transmitters, the magnetic communication, or a combination thereof may be gleaned from the teachings herein, including those of Paragraph Nos. 008-0014 and 0035-0055; and Figure Nos. 2-14 of U.S. patent application Ser. No. 13/251,493, filed on Oct. 3, 2011, incorporated by reference herein for all purposes regarding the encapsulation connector, the two or more transmitters, the magnetic communication, or a combination thereof. Alternatively, other teachings regarding rotating one or more of the tubes relative to each other may be gleaned from the teachings herein, including those of Paragraph Nos. 004-005, 0012-0038 and FIGS. 1A-4C of U.S. patent application Ser. No. 13/796,412, filed on Mar. 12, 2013, incorporated by reference herein for all purposes regarding a lock selector, bias device, and an actuation selector.

The outer tube, the inner tube, or both may be connected to a fluid source, a suction source, or both. In one example, a fluid may pass between the inner tube and the outer tube while suction passes though the inner tube. The inner tube may include one or more cutting features that remove and/or smooth material (e.g., tissue, cartilage, bone, ligaments, tendons, a cyst, the like, or a combination thereof) during a surgical procedure.

The inner tube, outer tube, intermediate tube, or a combination thereof may be rotatable, lockable, or both by a lock lever. Other teachings regarding the lock lever, components moved by the lock lever (e.g., locking spline), a collet, nosecone, internal gearing (e.g., pinion gears or nosepiece gears), or a combination thereof may be gleaned from the teachings herein, including those of Paragraph Nos. 005-007 and 0029-0054; and Figure Nos. 1-14 and related description in paragraph Nos. 0055-0070 of U.S. Patent Application Ser. No. 61/769,480, filed on Feb. 26, 2013, incorporated by reference herein for all purposes regarding a lock lever, components moved by the lock lever, the collet, the nosecone, and the internal gearing. Preferably, the lock lever is movably connected to the connection enclosure.

The inner tube may extend the full length of the interchangeable tip so that one end of the inner tube, opposite a cutting end, includes a drive attachment. The drive attachment may be any part of the inner tube that connects to a power transfer device, a coupler, a motor, a drive, or combination thereof so that the inner tube rotates. The drive attachment may be an integral part of the inner tube. The drive attachment may be a gear that is fixedly attached to the inner tube. The drive attachment may be a molded piece that is press fit around the inner tube so that the inner tube and the drive attachment move together. The drive attachment may connect with one or more parts of the tubeset discussed herein so that the tubeset assists in moving the inner tube during a procedure. The drive attachment once aligned with a tubeset, a motor, a handpiece, or a combination thereof may be locked into place.

he interchangeable tip may include one or more connecting tabs. The one or more connecting tabs may extend outward so that when the tabs align with an adjoining aperture (i.e., tip locking port) the connecting tabs extend into the aperture so that the interchangeable tip is fixedly connected to the adjoining part. The connecting tabs may be compressed so that the interchangeable tip is released from the adjoining part. As discussed herein the adjoining part may be a tubeset, a handpiece or both. Preferably, the interchangeable tip is locked directly to the handpiece via the connecting tabs extending through an aperture and/or port in the handpiece.

The handpiece may be any part of the device that is gripped by the user during use. The handpiece may be a central part of the device that assists in connecting or connects all of the pieces together so that the device functions as a surgical instrument. The handpiece may be a reusable part, a disposable part, or a combination thereof. Preferably, the handpiece is a reusable part that may be subjected to a sterilization process. More preferably, the handpiece may be free of parts that are subject to different coefficients of thermal expansion than the handpiece during sterilization. The handpiece may include one or more parts that have different coefficients of thermal expansion than the handpiece during sterilization. Preferably, the handpiece is free of components that may degrade through multiple sterilization cycles (e.g., repeated heating and cooling). More preferably, the handpiece is free of sealing components that may degrade through multiple sterilizations. The components of the handpiece may withstand about 500 or more, preferably about 1000 or more, or more preferably about 1500 or more sterilization cycles. The components of the handpiece may withstand about 5000 or less, about 3000 or less, or about 2500 or less sterilization cycles before the parts begin to degrade. The hand piece includes a front region, a center region, and a rear region.

The front region may be the part of the handpiece proximate to the interchangeable tip. The front region may be a part of the handpiece distal from where the handpiece is gripped during use. The front region includes one or more attachment ports. Preferably, the front region includes a tip attachment port and a power supply port. The tip attachment port may be any shape and size so that the tip attachment port accommodates the interchangeable tip. The tip attachment port may partially surround a portion of the interchangeable tip so that the tip is held securely in place by the tip attachment port. For example, the tip attachment port may be a "U" shape or a "C" shape so that the interchangeable tip is securely held by the tip attachment port and the interchangeable tip is substantially restricted so that the interchangeable tip is substantially free of movement. Preferably, the tip attachment port surrounds the interchangeable tip so that the tip attachment port completely encircles the interchangeable tip and restricts movement of the tip. The tip attachment port may be any shape that is complementary to the shape of the interchangeable tip. The tip attachment port may be a circle, square, diamond, a "D" shape, an ellipse, or a combination thereof so that the interchangeable tip is properly installed in the tip attachment port and the interchangeable tip is securely connected to the handpiece. The tip attachment portion may include one or more tip locking ports.

The tip locking ports may be located anywhere in the forward region of the handpiece. Preferably, the tip locking ports are located within the tip attachment port so that as the interchangeable tip extends into the tip attachment port the connecting tabs of the interchangeable tip extends into the tip locking ports and securely connects the interchangeable tip to the handpiece. The tip attachment ports may be an aperture, a through hole, a dimple, or a combination thereof in the handpiece. The tip attachment port may be any shape and size so that the tip attachment port accommodates and/or is complementary to the connecting tabs. The tip attachment port may be a circle, square, diamond, a "D" shape, an ellipse, or a combination thereof so that the interchangeable tip is fixedly connected to the handpiece. The front region in addition to the tip attachment port may include a power supply port.

The power supply port may be located anywhere in the front region so that during use power is supplied to the interchangeable tip. The power supply port is located below the tip attachment port. Preferably, the power supply port is located above the tip attachment port so that if any fluids leak the fluids would not leak into the power attachment port. The power supply port may assist in preventing rotation of the interchangeable tip relative to the handpiece. The interchangeable tip may include an active lead, a return lead, or both to provide for switching between monopolar tips, bipolar tips, neither, or a combination thereof. The active lead, the return lead, or both may be turned on, turned off, or both so that the microdebrider may be switched between bi-polar energy, mono-polar energy, or both. The active lead, the return lead, or both may be activated based on the configuration of the interchangeable tip, an electronic switch, or a combination thereof. Bipolar energy may deliver power to a centralized point of contact so that tissue is cauterized and fluids (e.g., blood) are coagulated during a procedure so that blood loss and pain is minimized after a procedure. The bipolar delivery may result in both an active lead and a return lead being located within the interchangeable tip so that the energy is only applied in a localized area. The monopolar delivery may include only an active lead, have only the active lead turned on, or both so that the active lead supplies power through the interchangeable tip, and the energy travels to a return lead which is located at a location other than the in the interchangeable tip (e.g., the return lead may be located on a patient's body). The monopolar energy may deliver power to a centralized point of contact so that tissue is cauterized and fluids (e.g., blood) are coagulated during a procedure so that blood loss and pain are minimized after a procedure. Monopolar energy may more efficiently provide power to a procedure site; however, bipolar energy may more accurately direct the energy. The interchangeable tip when fully connected may extend through the front region and into the center region.

The center region may be any part of the handpiece that is gripped during a procedure. The center region may be the largest portion of the handpiece. The center region may be free of any ports where other devices are inserted. Preferably, the center region includes a tubeset attachment port. The tubeset attachment port may be any feature that assists in coupling the tubeset to the handpiece. The tubeset attachment portion may be any device and/or feature that securingly connect the tubeset to the handpiece. Preferably, the tubeset attachment port may include a track so that the tubeset may be connected to the handpiece. The center region includes a track. The track may extend from a rear region through the entire length of the center region and terminate in and/or proximate to the front region. The center region may include a track on each side of the hand piece. The tracks may be substantially parallel. The tracks may slightly taper as the tracks extend from the rear end towards the front end. For example, the distance between the tracks may reduce by 1 micron or less for each mm of length of the track. The taper may be any amount of taper that assists in installing the tubeset in the handpiece. The taper on each side of the handpiece may be different. Preferably, the taper on each side of the handpiece is substantially the same. The tracks may taper so that the space in the center region is decreased when comparing the rear region to the front region. The tracks on each side may taper by about 5 degrees or more, about 8 degrees or more, about 10 degrees or more or about 11 degrees or more from a midline and/or midplane through the handpiece. The tracks on each side may taper by about 30 degrees or less, about 20 degrees or less, or about 15 degrees or less from a midline and/or mid-plane through the handpiece (i.e., about 12 degrees). The tracks may be comprised of one or more surfaces that connect an adjoining part to the handpiece. Preferably, the track includes an upper surface and a lower surface with a gap formed therebetween.

The lower surface may be a single planar surface. The lower surface may extend substantially the full length and width of the handpiece so that the lower surface forms a sliding surface for connecting with a tubeset. For example, during installation the tubeset will contact the lower surface and slide upon the lower surface so that the tubeset is connected with the handpiece. The lower surface may be any surface that assists in aligning and holding the tubeset in the handpiece. At least a portion of the lower surface is covered by the one or more upper surfaces.

Preferably, each of the upper surfaces extends over a portion of the lower surface on each side of the handpiece (e.g., a left upper surface and a right upper surface). The one or more upper surfaces may extend over the lower surface a sufficient amount so that a gap is formed between the upper surface and the lower surface and the tubeset slides through the gap to form a connection with the handpiece. The upper surface preferably is substantially the same width along the length of the upper surface. The thickness of the upper surface may vary from the front region to the rear region or vice versa. The thickness of the upper surface may vary so that the size of the gap formed between the upper surface and the lower surface changes. The thickness of the upper surface in the rear region and/or proximate to the rear region may have a thickness that is about 20 percent less, about 15 percent less, or about 10 percent less than the thickness of the upper surface in the front region and/or proximate to the front surface. The thickness may be stepped so that each of the upper surfaces become thicker and the gap reduced so that as the tubeset approaches the installed position alignment tolerances become tighter and the alignment of the tubeset relative to the handpiece and the interchangeable tip are decreased so that all of the pieces align.

The gap may vary due to the upper surface, the lower surface, or both being angled. The upper surface, the lower surface, or both may be angled so that the gap (i.e., distance between the two surfaces) is reduced. The thickness of the gap may become smaller from the rear region towards the front region or vice versa. Preferably, the gap becomes smaller under each of the upper surfaces when going from the rear region to the front region.

The upper surface may be one continuous piece. The upper surface may be about 2 pieces or more or preferably about 3 pieces or more. The upper surface may be about 10 pieces or less, about 7 pieces or less, or preferably about 5 pieces or less. Each piece of the upper surface may include a leading portion. The leading portion may be a side of each of the upper surfaces that faces the rear region of the handpiece. The leading portion may form any angle so that the tubeset may be connected to the handpiece. The leading portion may be tapered, angled, chamfered, or a combination thereof. The leading portion may form an angle that is sufficient so that the leading portion assists the user in connecting the tubeset to the handpiece. The leading portion may be a rounded corner, a chamfered corner, or both. The leading portion may form an angle of about 15 degrees or more, preferably about 25 degrees or more, or more preferably about 35 degrees or more with a side wall of the upper surface. For example, the upper surface may extend from an outside edge of the handpiece towards the center of the handpiece and the edge were the upper surface terminates towards the center is the side wall and the side wall may form an angle with the leading portion. The leading portion may form an angle of about 90 degrees or less, preferably about 75 degrees or less, more preferably about 65 degrees or less, or more preferably about 55 degrees or less (i.e., about 45 degrees) with a side wall of the upper surface. Each piece of the one or more upper surfaces of the handpiece may include a leading portion so that if tubeset while being moved from the rear region towards the front region of the handpiece encounters a recess the leading portion of the handpiece will assist the user in continuing to install the tubeset.

Preferably, the upper surface includes one or more recesses that assist in alignment, locking, ease of sliding, or a combination thereof. The upper surface will include a recess between each portion of the upper surface. The recess between each of the upper surfaces may be substantially the same size. The recess between each of the upper surfaces may vary in length. The recess may assist in locking the tubeset to the handpiece. For example, the tubeset may include one or more locking tabs that correspond to a recess so that once the tubeset is placed in the handpiece the locking tabs align with a recess and lock the tubeset in place. The recess in the upper surface may include a substantially vertical wall. The recess in the upper surface may include a bevel. The bevel may angle towards the opposing upper surface, away from the opposing upper surface, or both. Stated another way, the bevel may form an angle relative to a vertical portion of the track so that the bevel extends over the vertical portion, away from the vertical portion, or both. Preferably, the bevel is angled away from the opposing upper surface. The bevel may have an angle of about 1 degree or more, 2 degrees or more, or about 3 degrees or more. The bevel may have an angle of about 10 degrees or less, about 7 degrees or less, or about 5 degrees or less. The bevel may be angled so that the recess reduces contact with the tubeset, the rails, the locking tabs, or a combination thereof. A bevel may be located on a leading portion in the rear region of the handpiece to assist in guiding the tubeset into the track of the handpiece.

The rear region may include one or more drain ports. The drain ports may be any feature in the handpiece that allows fluids to exit the handpiece. Preferably, the drain port allows cooling fluids to exit the handpiece after the handpiece is removed from a cooling fluid. The drain ports may be located at any point in the handpiece, but preferably the drain ports are located in the rear region. Preferably, a drain port is located on each side of the handpiece. More preferably, the one or more drain ports are located proximate to the motor so that a motor cavity is flooded with a cooling fluid after heating and the cooling fluid is vacated after cooling. The drain ports may be configured so that cooling fluids can enter the handpiece but cannot pool in the handpiece. The drain ports may be located in the same cavity as a handpiece cap.

The rear region of the handpiece may include one or more handpiece caps that cover all or a portion of the motor, the motor power transfer device, or both so that the handpiece cap assists in guiding a tubeset into the track, prevents the tubeset from engaging the motor power transfer device during installation or both. Preferably, the handpiece includes only one handpiece cap. The handpiece cap may be any cover that partially and/or fully covers one or more components in the rear region. The handpiece cap may be any cover that is removable so that one or more components in the rear region are accessible. Preferably, once installed the handpiece cap is not removable. The handpiece cap may be any handpiece cap that assists in guiding a tubeset into the tracks of the handpiece. Preferably, the handpiece cap may assist in retaining the motor within the handpiece. More preferably, the handpiece cap assists is covering the motor power transfer device so that the motor power transfer device is not contacted and/or damaged when a tubeset is not installed. Most preferably, the handpiece cap provides the handpiece with aesthetically pleasing outer surface where the internal components are substantially hidden from view, but the components are not functionality impeded. The handpiece cap may cover a port that receives the motor.

The motor may be any motor that may be used to drive the interchangeable tip so that the microdebrider functions as a microdebrider. The motor may be any motor that rotates clockwise, counterclockwise, or both. The motor may be any motor that may be heated in an autoclave and sanitized. The motor may be any motor that may be rapidly heated and/or cooled without motor performance being affected. The motor may be heated and cooled without motor parts prematurely wearing, breaking, misaligning, or a combination thereof. The motor may be an enclosed motor so that the motor may be placed in a cooling fluid. For example, the motor may be placed in water and the water may not penetrate the outer surface of the motor damaging the internal components. The motor may be any motor that rotates in a single direction at a rate of about 5,000 revolutions per minute (RPM) or more, preferably at rate of about 10,000 RPM or more, more preferably at a rate of about 12,000 RPM or more, and most preferably at a rate of about 14,500 RPM or more. The motor may be any motor that rotates in a single direction at a rate of about 30,000 RPM or less, about 20,000 or less, or about 17,000 RPM or less (i.e., about 15,000 RPM). The motor may be any motor that oscillates (i.e., rotates in a first direction and then in a second direction) at a rate of about 1,000 RPM or more, about 2,500 or more, or about 4,500 RPM or more. The motor may be any motor that oscillates at a rate of about 10,000 RPM, about 7,500 RPM, or about 6,000 RPM. One that may be used is a brushless DC motor, available from Portescap. The motor may be substantially sealed within the handpiece so that the handpiece protects the motor from fluids. The motor may be sealed within the handpiece so that only an end of the motor and/or a portion of an end of the motor is not covered by the handpiece. The motor may be sealed within the handpiece so that the motor power transfer device extends out of the handpiece.

The motor power transfer device may be any power transfer device that may transfer power from the motor to another component so that the other component rotates. The motor power transfer device may be any power transfer device that directly couples to another power transfer device so that the power transfer device is rotated. The motor power transfer device may directly connect to another component so that the other component is directly driven by the motor power transfer device. Preferably, the motor power transfer device transfers power to a second power transfer device that drives a component. The motor power transfer device may be belt and pulley, a cog, a gear, a sprocket, a toothed wheel, or a combination thereof. The motor power transfer device may be any power transfer device that may be heated and cooled. The motor power transfer device may be any power transfer device that may substantially maintain its shape, form, structural attributes, tolerances, or a combination thereof when rapidly heated and cooled. The motor power transfer device may be made of a natural material, a synthetic material, a metal, a plastic, a polymer, or a combination thereof. Preferably, the motor power transfer device is made of metal. The motor power transfer device and motor may be located proximate to a power attachment port.

The power attachment port may be located in any location in the handpiece so that a power attachment provides power to the microdebrider through the power attachment port. The power attachment port may be located anywhere in the handpiece so that power may be provided to the motor, the interchangeable tip, or both. Preferably, the power attachment port is located in the rear region of the handpiece. More preferably, the power attachment port is located in the rear region of the handpiece below both the motor and the motor power transfer device. The power attachment port may be located so that the power attachment extends into the handpiece and does not interfere with a user's hand positioning. Stated another way, the power attachment port may be located so that a user may ergonomically grip the microdebrider so that hand strain is minimized. The power attachment port may include an attachment and/or detachment feature so that the power attachment may be connected and disconnected from the handpiece so that the handpiece may be sanitized after use. The power attachment port may be angled so that the power attachment port rests on a user's hand during use, the handpiece curves to the shape of a hand, the power attachment forms an angle so that the power attachment is aligned with a user's hand and/or arm so that the weight of the power attachment is not supported solely by the user's grip. The power attachment port may be located at any location so that the power attachment port, the power attachment, or both do not interfere with the tubeset being connected to the handpiece.

The tubeset may be any tubeset that connects one or more tubes to the microdebrider, includes one or more power transfer devices, is disposable, provides power to an interchangeable tip, or a combination thereof. The tubeset may be any device that forms a connection with the handpiece. The tubeset may form any connection with the handpiece so that the tubeset, handpiece, interchangeable tip, or a combination thereof align, lock in place, have a driving relationship (e.g., a motor powers one or more of the components in series). The tubeset may include one or more alignment features so that the tubeset, the handpiece, the interchangeable tip, or a combination thereof align and form a fixed connection.

The one or more alignment features may be any feature that aligns the tubeset and the handpiece, the interchangeable tip and the handpiece, the interchangeable tip and the tubeset or a combination thereof. The one or more alignment features may be rails, a part formed on the rails, or both. The rails may be any part of the tubeset so that the tubeset forms a fixed connection with the handpiece, the interchangeable tip, or both. The rails may be any part of the tubeset so that the tubeset is aligned with the handpiece, the interchangeable tip, or both. Preferably, the rails are a part of the tubeset that assists the tubeset in self-aligning during installation of the tubeset to the handpiece. The rails may be located at any location on the tubeset so that the tubeset connects to the handpiece, the interchangeable tip, or both. Preferably, the rails are located on a bottom portion of the tubeset so that the rails assist in forming a connection with the handpiece, the interchangeable tip, or both. More preferably, the rails extend laterally from the tubeset. The rails may be any part of the tubeset that forms a complementary fit with the tracks of the handpiece. The one or more rails may be substantially planar (e.g., the rails extend along a single plane).

The one or more rails may extend at an angle relative to a plane. For example, the rails may extend outward from a centerline that bisects the tubeset along an axis, the rails at the axis have a plane, and as the one or more rails extend outward from the centerline the rails extend out of the plane. Some of the one or more rails may extend above the plane, below the plane, along the plane, or a combination thereof. The one or more rails may form an angle of about 0.1 degrees or more, about 0.5 degrees or more, about 1 degree or more, or about 2 degrees or more with a plane. The one or more rails may form an angle of about 5 degrees or less, about 4 degrees or less, or about 3 degrees or less with the plane, but greater than 0 degrees. The rails may include one or more alignment features that assist the rails in self-aligning the tubeset on the handpiece.

The one or more alignment features may be any feature that assists in self-aligning the tubeset, elevating the tubeset above the handpiece so that an air gap is formed between the tubeset and the handpiece, reducing heat transfer between the motor in the handpiece and the tubeset, or a combination thereof. Preferably, the one or more alignment features are one or more bumps, one or more surfaces, one or more reliefs, one or more cutouts, or a combination thereof located on the one or more rails.

The one or more bumps may be any feature that creates a contact surface on a rail. The one or more bumps may be any feature that is elevated above and/or extends out from a surface of the rail. The one or more bumps may be a feature that forms a contact point on one or more of the rails. The one or more bumps may reduce the surface area of the rails in contact with the tracks so that the amount of force to install the tubeset is reduced. For example, the one or more bumps may be a feature that is elevated above and/or out from the rails so that during installation and/or removal the one or more bumps contact an opposing surface first and/or are the only surface of a rail to contact an opposing surface. In another example, a bump elevates above a rail so that during installation the bump contacts a bottom side of an upper surface of a track so that the bump prevents the tubeset from being inserted at an angle where the components of the tubeset do not align.

The one or more bumps may be any size and shape so that the one or more bumps assist the tubeset in aligning during installation; so that the one or more spring rails are deflected during installation; so that a friction fit, an interference fit, or both are created when the rails are fully inserted; so that the bumps deflect the one or more rails in the direction of a relief and/or cutout, or a combination thereof. The one or more bumps may be a point (i.e., the length and width are substantially equal) on the one or more rails; a line (i.e., the length is larger than the width); or both. The one or more bumps may be a half sphere, a half-cylinder, geometric, non-geometric, linear, non-linear, square rectangular, tubular, triangular shaped, shark fin shaped (e.g., a rounded forward portion and a straight rear portion), or a combination thereof. The one or more bumps may be located at any location on the rails. The one or more bumps may be located on a forward portion, a rear portion, a side edge, a top, a bottom, or a combination thereof of the one or more rails. Preferably, the one or more bumps are located on the top of the rails, the side edges of the rails, or both. The one or more bumps may have any dimension that assists the tubeset in self-aligning in the tracks. Preferably, the one or more bumps have a height (e.g., measured from a surface of the rail to the highest point of the bump) of about 0.001 mm or more, about 0.01 mm or more, or about 0.1 mm or more. The highest point of the one or more bumps may be about 2 mm or less, about 1 mm or less, or preferably about 0.5 mm or less. The one or more rails may include one or more surfaces that oppose the one or more bumps, that are located on different rails than the bumps, are located adjacent to the one or more bumps, or a combination thereof.

The one or more surfaces may be any surface that assists in aligning the tubeset during installation. The one or more surfaces may perform any of the functions discussed herein for the bumps. The one or more surfaces may be any surface that is elevated from a surface of the rails. The one or more surfaces may assist in alignment, in creating a friction fit, in flexing the one or more spring rails, or a combination thereof. The one or more surfaces may be any elevated feature that extends from a rail. Preferably, the one or more surfaces have a lower profile than a bump (e.g., a height of the bump is greater than the height of a surface when measured from the rail to the highest point of the bump and/or surface). More preferably, the one or more surfaces are located on a bottom surface of the one or more rails so that during installation the surfaces contact the handpiece, the surfaces elevate the rails so that the rails can be deflected, or both. The one or more surfaces may be any shape and/or size so that the one or more surfaces assist in self-aligning the tubeset to the handpiece and/or interchangeable tip during installation, the rails may deflect during installation, the rails form a friction fit within the tracks, the surfaces reduce the surface area in contact with the handpiece, the surfaces are the only portion of the rails in contact with the handpiece, the rails that do not include a surface are substantially free of contact with the handpiece, or a combination thereof. The one or more surfaces may be square shaped, round, rectangular, a point, a line, linear, non-linear, geometric, non-geometric, shark fin-shaped, or a combination thereof.

The thickness of the one or more surfaces may be substantially constant along the length of each surface; the thickness of the one or more surfaces may vary along the length of the one or more surfaces; increase in thickness as the one or more surfaces extend outwards (e.g., the rails may be substantially free of surfaces along a line that bisects the tubeset along the tubeset axis and as the rails extend away from the axis a height of the one or more surfaces may become larger). The thickness (i.e., the distance each surface extends above and/or below the rails) of the one or more surfaces may be any height so that the one or more surfaces perform the functions discussed herein. The thickness of the one or more surfaces may be about 1 mm or less, preferably about 0.5 mm or less, or about 0.3 mm or less. The thickness of the one or more surfaces may be more than about 0 mm, about 0.001 mm or more, about 0.005 mm or more, about 0.01 mm or more, or about 0.05 mm or more. For example, the surface may have a thickness of about 0 mm along the centerline and a thickness of about 0.2 mm or more at a distal point on the one or more rails. The thickness of the one or more surfaces may be any surface so that the surface extends along a plane to compensate for an angle of the rails extending out of the plane, so that the surface elevates one or more adjacent rails so that the rails may defect towards a relief and/or a cutout formed in a rail, so that a spring rail may deflect, or a combination thereof.

A relief and/or cutout may be any feature on and/or within a rail that allows the rail to deflect during installation, removal, or both. A relief, a cutout, or both may be an absence of material. For example, a relief may be a location on a rail where material was removed and/or the rail was formed so that material is not present in a location on the rail, or both. A relief, a cutout, or both may form an angle in and/or on a surface of the one or more rails that allows the one or more rails to extend in the direction of the respective relief, a cutout, or both. A relief, a cutout, or both may be any feature in and/or on the one or more rails that assists in self-aligning the tubeset during installation. A relief, a cutout, or both may be present on any rail. Preferably, a relief, a cutout, or both are only present on spring rails. For example, the relief, the cutout, or both may allow the rail space so that when a surface and/or a bump contacts a wall of the handpiece the rail may move in the direction of the relief, the cutout, or both. The relief, the cutout, or both may be an angled portion on and/or in one or more surfaces of the rails so that the rail deflects when pressure is exerted on the rail.

The relief, the cutout, or both may be any size and shape so that the relief, the cutout, or both assist in self-aligning the tubeset with the handpiece, the interchangeable tip, or both; so that the rails move during installation; so that the rails deflect and form a friction fit when the rails are completely installed; or a combination thereof. The relief, the cutout, or both may be configured so that the remaining portion of the rail includes a shape that is angled, linear, triangular, geometric, non-geometric, rounded, angled away from a bottom wall, angled away from a top wall, angled away from a side wall, shark finned-shaped, or a combination thereof. Preferably, the relief is an angled portion on a bottom side and/or top side of a rail so that the rail deflects up and/or down during installation so that the deflection of the rail assists in self-aligning the rails within the track along a vertical direction. Preferably, the cutout is an absence of material in a rail between the distal end of the rail and the centerline, and the cutout allows the rail to deflect laterally from side to side during installation so that the rail assists in self-aligning the rails within the tracks along a horizontal direction. The relief, the cutout, or both may be present only on spring rails.

A spring rail may be any rail that deflects during installation. A spring rail may be any rail that assists the tubeset in self-aligning. A spring rail may be any rail that moves and/or is movable during installation. A spring rail may be any rail that does not contact one or more surfaces of the handpiece during installation. A spring rail may move vertically, horizontally, or both during installation. A spring rail may move during installation so that the spring rail assists in creating a friction fit, to accommodate a taper in the track (i.e., where the track narrows), or both. The spring rails may move a sufficient amount so that the spring rails assist in self-aligning the tubeset; forming a friction fit; elevating all or a portion of the tubeset, the drive shaft, the drivetrain; or a combination thereof above the handpiece; or a combination thereof. The one or more spring rails may require a sufficient amount of force to move so that the spring rail assists in creating a friction fit; accommodates a taper in the track, assists in self-aligning the tubeset; forming a friction fit; elevating all or a portion of the tubeset, the drive shaft, the drivetrain, or a combination thereof above the handpiece; or a combination thereof. The spring rails may move about 10 microns or more, about 20 microns or more, preferably about 30 microns or more, or more preferably about 40 microns or more (i.e., about 50 microns). The spring rails may move about 2 mm or less, about 1 mm or less, about 0.8 mm or less, or about 0.6 mm or less. The tubeset may include spring rails in a leading portion, a central portion, a trailing portion, or a combination thereof. The tubeset may include spring rails in a forward position, a rear position, or both. The rear portion, the forward portion, or both may include leading spring rails, central spring rails, trailing spring rails, or a combination thereof so that the spring rails assist in aligning the tubeset during installation. The spring rails may move up, down, towards a centerline, or a combination thereof. The spring rails may move so that the one or more locking tabs on the cover of the tubeset align with a recess in the handpiece so that the tubeset is securely connected to the handpiece.

The cover may be any cover that protects the parts of the tubeset, locks the tubeset to the handpiece, or both. The cover may be any cover that assists in aligning the tubeset to the handpiece, the interchangeable tip, or both. The cover may include one or more ports so that fluid lines, a positioning system, an image guidance system, power lines, or a combination thereof may be connected to the microdebrider during use. The positioning system port and/or image guidance port may be any port so that a positioning system, an image guidance system, or both may be connected to the microdebrider for use during a procedure. The positioning system port and/or image guidance system port may be configured so that a variety of positioning equipment and/or image guidance systems may be used in conjunction with the device taught herein. The positioning system may be any positioning system that assists in surgery, assists in positioning the interchangeable tip relative to another device, an organ, or both. The image guidance system may be any image guidance system that may assist in tracking the tip or the entire length of the microdebrider during a procedure, guiding the interchangeable tip to a site of interest, or both.

The cover may include one or more locking tabs. Preferably, the locking tabs are on opposing sides of cover and the locking tabs correspond to one or more recesses in the handpiece. The one or more locking tabs may be flexible so that the one or more locking tabs may slide through the tracks, the recesses in the tracks, or both so that the locking tabs assist in locking the cover to the handpiece, axially aligning the cover on the handpiece, or both. The locking tab may create a force on each side of the handpiece so that the tubeset cover is axially aligned relative to the drivetrain during installation of the tubeset on the handpiece. The one or more locking tabs may be configured so that the locking tabs may be moved only in a single direction without the locking tabs being depressed by an external force. For example, the locking tabs may be inserted into the handpiece in an insertion direction and the locking tabs may be depressed by contact with the handpiece, but the locking tabs may prevent retraction from the handpiece in a retraction direction without the locking tabs being actuated and/or depressed. The locking tabs may be of any size and shape so that the locking tabs may be inserted into the handpiece and prevent retraction and/or assist in alignment. The locking tabs may have a locking piece that extends off of the locking tabs into the recess of the handpiece. The locking piece may have an insertion side and a retraction side. The locking tabs may have an insertion side that is curved, rounded, tapered, angled, shark fin shaped, the like, or a combination thereof so that when a locking tab contacts a recess, a track, or both the locking tab is actuated so that the tubeset can be inserted into the handpiece. The insertion side may assist the locking tabs in attaching the tubeset in the direction of attachment of the tubeset. The locking tabs may have a retraction side that is flat, square, non-rounded, non-angled, the like, or a combination thereof so that the locking tab contacts a recess and prevents retraction of the tubeset. The locking tabs may be flexible so that the locking tabs may be actuated to move around the recesses so that the tubeset may be removed from the handpiece, installed in the handpiece, or both. The locking tabs may be flexible pieces that are an integral part of the cover, and extend from the cover so that the locking tabs are movable. The cover may include a rear plate.

The rear plate may be any plate that assists in aligning the tubeset with the handpiece, coupling one or more fluid tubes to a corresponding part on a drivetrain, seals the one or more fluid lines in the cover, or a combination thereof. The rear plate may include one or more seals that assist in preventing leakage at a connection formed proximate to the rear plate. The rear plate may include a rear plate alignment projection. The rear plate alignment projection may extend along an axis of the drivetrain so that the rear plate assists the tubeset in aligning with a rear end of the handpiece. The rear plate alignment projection may be any part that extends along an axis of the drivetrain and into a corresponding alignment port in the handpiece so that the tubeset and the handpiece are aligned. The rear plate alignment projection may extend out from a rear end of the tubeset a sufficient distance so that the projection assists in aligning the tubeset to the handpiece and assists in preventing lateral movement of the tubeset when in the installed position. The rear plate alignment projection may extend out from a rear end of the tubeset a distance of about 1 mm or more, about 2 mm or more, or about 3 mm or more. The rear plate projection may extend out from a rear end of the tubeset a distance of about 10 mm or less, about 7 mm or less, or about 5 mm or less. The rear plate may include one or more ports.

The rear plate may include one or more ports and/or one or more seals that assist in sealing one or more fluid lines into the tubeset so that the one or more fluid lines may provide a fluid and/or remove a fluid. The rear plate may be a bridge between one or more fluid lines that are located outside of the tubeset and the fluid lines that extend through the tubeset so that fluids may be provided to and/or removed from the interchangeable tip. The one or more ports may form a sealed connection between an external fluid line and an internal fluid line. The rear plate may be removably attached to the cover so that a separate fluid line may be extended through the rear plate and connected to the drivetrain and the rear plate placed over the connection so that the connection is secured by the rear plate. The rear plate may assist in securing a portion of the drivetrain in the tubeset. The rear plate and cover may be made of different materials. Preferably, the rear plate and the cover are made of the same material. The rear plate and cover may be made of any material that may assist in aligning the tubeset in the handpiece that assists in holding one or more tubes in the tubeset, assists in sealing the one or more tubes to a bridge, or a combination thereof. The rear plate and cover may be made of a natural material, a synthetic material, a metal, a polymer, a plastic, or a combination thereof. Preferably, the rear plate is made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. More preferably, the rear plate and cover are made of polycarbonate. The rear plate may secure an end of the drivetrain in the cover and the cover may secure the rest of the drivetrain in the cover.

The cover may include one or more attachment features that secure the drivetrain in the cover. The attachment features may be any feature that secures the drivetrain in the cover so that the cover protects the drivetrain, covers the drivetrain, assists in locking the drivetrain to the handpiece, or a combination thereof. The cover may include a forward attachment feature, a central attachment feature, a rear attachment feature, or a combination thereof. The one or more attachment features may be any feature that connects the tubeset in the cover. The attachment feature may be a post, a gripper, a hook, a snap feature, a welded connection, a glued connection, a fastener, or a combination thereof. The cover may include a post that is gripped by the drivetrain and a gripper that grips a portion of the drivetrain. Preferably, the attachment feature is a post and the drivetrain includes a corresponding gripper that connects to each side of the post so that a secured connection is formed. The gripper may form a friction fit, an interlocking fit, may grip a projection on the post, may form an interference fit, or a combination thereof. The one or more attachment features may be positioned around the drivetrain so that the drivetrain is held in place and is substantially free of movement when installed. The one or more attachment features may partially surround the drivetrain to assist in preventing the drivetrain from moving independent of the cover. Preferably, the drivetrain is securely fixed to the cover so that the drivetrain is fixedly attached to the handpiece, the interchangeable tip, or both when the drivetrain is fully installed.

The drivetrain may have any configuration so that when installed the drivetrain assists in providing a fluid, power, removing a fluid, a driving force, or a combination thereof to and/or from the interchangeable tip. The drivetrain may be made of any material so that the drivetrain assists in transferring heat, prevents heat transfer, is resistant to the fluids used with the tubeset, may withstand the rotational speeds of the drive shaft, the bearings, the washers, or a combination thereof. The drivetrain may be made of a natural material, a synthetic material, a metal, a polymer, or a combination thereof. The drivetrain may be made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. Preferably the drivetrain may be made of polycarbonate or acetal. The drivetrain may couple a motor to an interchangeable tip so that the drivetrain transfers power from the motor to the interchangeable tip. The drivetrain may include one or more power transfer devices. The one or more power transfer devices may form a connection with a motor power transfer device so that power is transferred from the motor through the power transfer devices to the interchangeable tip so that the interchangeable tip rotates. The one or more power transfer devices may be any device that may couple to a motor so that the motor provides power through the power transfer device. The power transfer device may be a belt and pulley, a sprocket, a gear, a cog, the like, or a combination thereof. Preferably, the power transfer device is a toothed gear. The power transfer device may be connected to a drive shaft so that power provided by the motor is transferred to the interchangeable tip through the power attachment device and the drive shaft.

The drive shaft may be any device that receives power at one end and drives a device at an opposing end. The drive shaft may be connected within the drivetrain. The drive shaft may be moveably connected in the drivetrain. Preferably, the drive shaft is movable along the rotational axis of the drive shaft. More preferably, the drivetrain is movable along the rotational axis of the drivetrain so that during installation the power transfer device may contact the motor power transfer device and form a connection. The drive shaft may be movable along the rotational axis of the drive shaft so that the power transfer device of the drive shaft self-aligns with a motor power transfer device when the tubeset is fully installed on the handpiece. The drive shaft may be any shaft that has sufficient strength to withstand a rotational torque, to withstand rotational speeds as discussed herein (e.g., up to 15,000 PRM or more), corrosion resistance, resistance to fluids and materials typical to those a microdebrider is subjected, or a combination thereof. The drive shaft may be any shape and size so that the drive shaft may provide power so that the interchangeable tip is rotated. The drive shaft may be a solid piece, a hollow piece, round, cylindrical, or a combination thereof. Preferably, the drive shaft is a hollow tube. The drive shaft may be made of any material that has sufficient strength to rotate the interchangeable tip, has good heat transfer characteristics, in an insulator, is abrasion resistant, can withstand the rotational speeds discussed herein, or a combination thereof. The driveshaft may be made of a natural material, a synthetic material, a metal, a polymer, or a combination thereof. The drive shaft may be made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. Preferably, the drive shaft may be made of stainless steel. The drive shaft may ride on one or more bearings, one or more washers, one or more seals, or a combination thereof.

The tubeset may include one or more washers at any location within the tubeset. The one or more washers may be located around the drive shaft. The one or more washers may assist in spacing the bearing, the coupler, the power transfer devices, or a combination thereof. Preferably the one or more washers are located proximate to the coupler and the bearings. The one or more washers may be located proximate to one or more seals. The one or more seals may be located within any connection point so that fluid leakage is prevented loss of suction is prevented, or both. The one or more seals are preferably located near and/or in the coupler, on both ends of the drive shaft, in the coupler, on the ends of the fluid bridges, or a combination thereof. The one or more seals may be made of any material that assists in preventing fluid leakage, is resistant to heat, is resistant to the fluids used with the microdebrider, prevents loss of suction, or a combination thereof. The one or more seals may be made of a natural material, a synthetic material, a metal, a polymer, or a combination thereof. The seals may be made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. Preferably the seals may be made of silicone.

The one or more bearings may be any bearing that extends around a circumference of the drive shaft so that the bearings allow the drive shaft to rotate around its rotational axis. The one or more bearings may be any bearing that may withstand a rotational speed of about 15,000 RPM in a single direction, a rotational speed of 5,000 RPM in a first direction and then in a second direction (i.e., oscillates), or both. The one or more bearings may be a low friction polymeric material that extends around a circumference of the drive shaft and assists the drive shaft in being rotated by the motor. The bearings may be located at any location along the length of the drive shaft. The bearings may form a fixed connection (i.e., the bearings may rotate with the drive shaft and the outside of the bearings contact an opposing surface) with the drive shaft, a loose connection (i.e., both the drive shaft and the bearings rotate during use and the rate of rotation of the bearings may vary relative to the drive shaft) with the drive shaft, or a combination thereof. Preferably, the bearings and the drive shaft are in close proximity. The inner diameter of the bearings and the outer diameter of the drive shaft may have a close relationship so that the bearing, under normal loading, stabilize and support the drive shaft, the blade tip, or both. The inner diameter of the bearings and the outer diameter of the drive shaft may have a diametric relationship of about 0.5 mm or less, preferably about 0.1 mm or less, or more preferably about 0.08 mm or less. The inner diameter of the bearings and the outer diameter of the drive shaft may have a diametric relationship of about 0.001 mm or more, about 0.005 or more, or about 0.01 mm or more. The bearings and washers may be made of any material that forms a low friction surface, that assist the drive shaft in rotating, that can withstand the rotational speeds of the drive shaft, that can operate within a high temperature range, or a combination thereof. The one or more bearings, the one or more washers, or both may be made of a natural material, a synthetic material, a metal, a polymer, or a combination thereof. The bearings and washers may be made of ethylene vinyl acetate (EVA), polyethylene vinyl acetate (PEVA), polyvinyl acetate (PVA), polyvinyl butyral (PUB), plastic, a polyvinyl chloride (PVC), a polytetrafluoroethylene (PTFE), a polyester, a polyvinyl fluoride (PVF), a polycarbonate, acetal, or a combination thereof. Preferably the bearings and washers may be made of polytetrafluoroethylene. A bearing may assist in coupling the driveshaft to the interchangeable tip.

Preferably, a coupler may be connected to the drive shaft proximate to an end of the drive shaft (e.g., distal end of the shaft or front region of the device). The coupler may be any device so that the coupler connects the drive shaft to the interchangeable tip so that the drive shaft provides power to the interchangeable tip. The coupler may be fixedly connected to the drive shaft and may include a port so that a portion of the interchangeable tip may be inserted into the port and/or around the port to create a fixed connection. Preferably, the coupler surrounds a portion of the interchangeable tip so that the drive shaft and the interchangeable tip form a connection so that power provided by the motor drives the interchangeable tip. The coupler may be a fitting between the interchangeable tip and the drive shaft so that fluids may pass through the drive shaft. The coupler may be made of any material that assists in: creating a rotational connection between the interchangeable tip and the drive shaft, forming a sealing connection, may withstand the rotational speed of the drive shaft and the interchangeable tip, or a combination thereof. The one or more couplers may be made of a natural material, a synthetic material, a metal, a polymer, or a combination thereof. The coupler may be made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. Preferably the coupler may be made of a polycarbonate. Preferably, the coupler assists in creating an substantially sealed connection so that fluids pass from and/or to the interchangeable tip, through the drive shaft, and out and/or in through a fluid line and/or a suction line. The coupler may include one or more seals so that a sealed connection is formed between the coupler and the one or more fluid lines, one or more suction lines, or both.

The one or more fluid lines may be any fluid line that assists in carrying a fluid from and/or to the interchangeable tip. The one or more fluid lines may connect to the tubeset, extend through the tubeset, partially extend through the tubeset, or a combination thereof. The one or more fluid lines may extend through the tubeset at any location. Preferably, the one or more fluid lines extend through the tubeset so that the fluid passing through the fluid lines cools the one or more bearings of the tubeset, cools the handpiece so that heat from the motor is not transferred to the tubeset, cools the tubeset, or a combination thereof. Preferably, the one or more fluid lines extend to the rear of the tubeset, through the rear plate, or both.

The one or more fluid lines may be made of any material with high heat transfer properties, with low heat transfer properties, has a high abrasion resistance, a low abrasion resistance, high flexibility, or a combination thereof. The one or more fluid lines may be made of a natural material, a synthetic material, a metal, a polymer, or a combination thereof. The one or more fluid lines may be made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. Preferably, the one or more fluid lines are made of polyvinyl chloride (PVC). The one or more fluid lines may connect to a bridge that assists in allowing the fluids to pass through the tubeset. The one or more fluid lines may connect the bridge via one or more ports. The one or more ports may assist in forming a sealed connection with each respective bridge and fluid line. The tubeset may include one or more fluid line supports that support the fluid lines that extend into and/or though the tubeset. Preferably, the one or more fluid line supports assist in guiding one or more fluid lines around a power transfer device. Most preferably, the tubeset includes a fluid attachment port and a suction attachment port where a fluid (e.g., sterile water or saline) is supplied through a rear region of the tubeset and into the interchangeable tip so that water is provided during a procedure, and suction is supplied through the rear region of the tubeset connecting with a suction bridge that provides suction to the interchangeable tip so that material may be removed during a procedure.

The suction bridge may be the hollow portion of the drive shaft so that as the drive shaft rotates material is moved through the drive shaft and removed. In one non-limiting example, the tubeset includes a fluid port in an upper portion of the rear region; a fluid line extends through the fluid port over the power transfer device and connects to the fluid bridge via the fluid attachment; and the fluid bridge, on the opposing side, connects to the interchangeable tip so that fluid is provided during a procedure. In another non-limiting example, a suction line extends to a suction port; the suction port is also a suction attachment that connects the suction line to the suction bridge (i.e., the drive shaft); and the drive shaft connects to the interchangeable tip via the coupler forming a fluid connection so that materials may be removed during a procedure.

The device as taught herein may be connected using a connection method. The connection method may include one or more of the following steps performed in virtually any order: aligning the tubeset with the tracks in the handpiece; sliding the tubeset rails into the tracks of the handpiece; pushing the tubeset until the locking tabs connect with handpiece; aligning the interchangeable tip with the handpiece; pushing the interchangeable tip until the interchangeable tip locks on the handpiece; connecting a power supply to the handpiece; connecting a suction line; or connecting a fluid line.

FIG. 1 illustrates a front perspective view of a microdebrider 2 being assembled. The microdebrider includes a tubeset 70 and the tubeset 70 is being connected to a handpiece 40. The tubeset 70 has rails 72, a suction attachment 74, and a drivetrain 100. The rails 72 correspond to tracks 44 in the handpiece 40 so that the tubeset 70 and the handpiece 40 are aligned. The tracks 44 include one or more recesses 68 for locking the tubeset 70 to the handpiece 40. As illustrated the recesses 68 include a bevel 69 angled away from a center line 200 extending through the center of the handpiece 40 so that the handpiece 40 is separated into two substantially equal portions. The handpiece 40 includes a power supply line 42 for powering the microdebrider 2. The handpiece 40 includes a tip attachment port 54 and a power supply port 57 on a distal end of the handpiece 40 for attachment to a interchangeable tip 10 that includes a stylet 12. The handpiece 40 includes a drain port 47 so that fluids that may enter the handpiece 40 can exit the handpiece 40.

Figure 2:
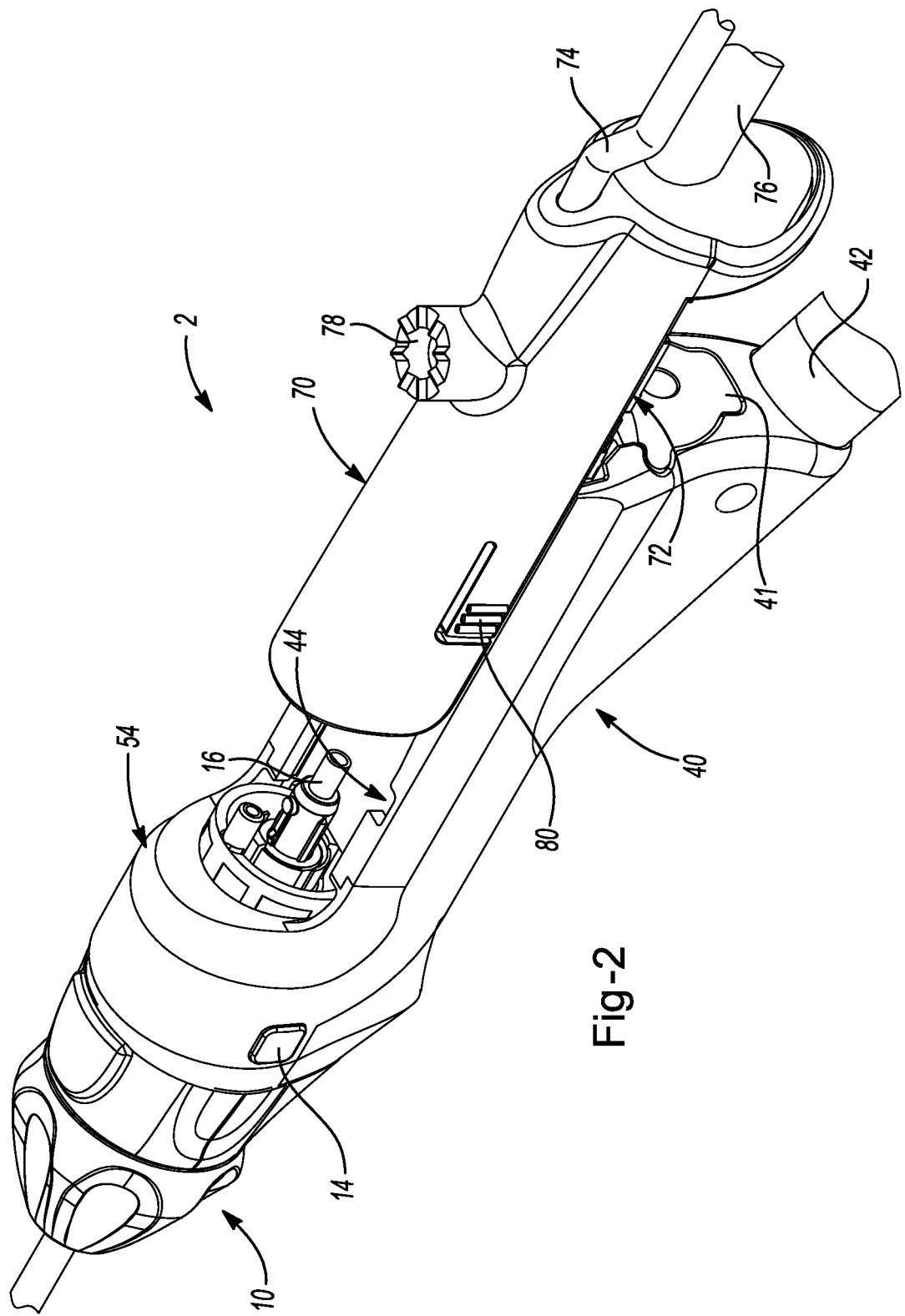
FIG. 2 illustrates a rear perspective view of FIG. 1.

FIG. 2 illustrates a rear perspective view of a microdebrider 2 being assembled. As illustrated the tubeset 70 is slidably connected to the handpiece 40. The handpiece 40 includes a handpiece cap 41 that covers the motor power transfer device 106 (not shown). The tubeset 70 includes an image guidance attachment post 78 in the top of the tubeset 70, a fluid attachment 74 in the upper rear region of the tubeset 70, and a suction attachment 76 in a central rear region of the tubeset 70. The tubeset 70 includes rails 72 that align with corresponding tracks 44 in the handpiece 40 to assist in properly aligning the tubeset 70 with the handpiece 40, and locking tabs 80 that assist in aligning and locking the handpiece 40 and the tubeset 70 together so that once they are properly aligned the position is maintained. The handpiece 40 includes a power supply line 42 for powering the motor (not shown) so that the motor (not shown) can supply power to the interchangeable tip 10 via the drivetrain 100 (not shown). The interchangeable tip 10 connects to the handpiece 40 via the tip attachment port 54. As is illustrated, the drive attachment 16 of the interchangeable tip 10 extends through the tip attachment port 54 so that the drive attachment 16 connects to the drivetrain 100 (not shown) so that power is supplied to the interchangeable tip 10. The interchangeable tip 10 is attached to the handpiece 40 by connecting tabs 14 on opposing sides of the handpiece 40.

FIG. 3 illustrates a cross-sectional side view of an assembled microdebrider 2. A front region of the microdebrider 2 includes a interchangeable tip 10. The interchangeable tip 10 includes a drive attachment 16 that extends though the handpiece 40 and connects to the drivetrain 100. The drivetrain 100 includes a coupler 102 that connects to the drive attachment 16 so that the drivetrain 100 supplies power to the interchangeable tip 10. The drivetrain 100 includes a power transfer device 104 that is moved by the motor 46. The drivetrain 100 includes bearings 94 that allow the drivetrain 100 to rotate so that the drivetrain 100 provides power to the interchangeable tip 10 via the drive attachment 16. The tubeset 70 includes a fluid port 92 in a rear end region that connects to a fluid line 90 so that a fluid can pass through a fluid bridge 88 in the tubeset 70 and into and/or out of the interchangeable tip 10. The tubeset 70 includes a suction port 86 in a rear end region that connects to a suction line 84 so that a suction can be applied and material moved through the interchangeable tip 10 into a suction bridge 82 and out the tubeset 70 into the suction line 84. The suction bridge 82 as illustrated includes the bearings 94 on a front end for connecting to the drive attachment 16 and a bearing 94 on the rear end for connecting to the power transfer device 104 so that the suction bridge 82 assists in transferring rotational power from the power transfer device 104 and motor 46 to the interchangeable tip 10. The handpiece 40 includes a power attachment port 48 for connecting the handpiece 40 to a power supply line 42, which provides power to the motor 46 and the interchangeable tip 10 via the power supply port 57. The motor 46 when powered rotates the power transfer device 50 that is connected to and rotates the power transfer device 104 in the drivetrain 100. The power transfer device 104 transfers rotational power through the suction bridge 82 to the drive attachment 16 so that the interchangeable tip 10 can be used to cut. The tubeset 70 includes an image guidance port 78 so that an image guidance system (not shown) can assist in the use of the microdebrider 2.

FIG. 4 illustrates a perspective view of one example of a handpiece 40. The handpiece 40 includes a tip attachment portion 54, tip locking ports 56, and power supply port 57 in a front region 58 of the handpiece 40. The central region 60 of the handpiece 40 includes a tubeset attachment port 52 for receiving a tubeset (not shown). The rear region 62 of the handpiece 60 includes tracks 44 that extend from the rear region 62 into the central region 60 so that a tubeset can attach to the handpiece 40. The rear region 62 includes a power transfer device 50 and a power attachment port 48 for connecting to a power supply line 42 (not shown).

Figure 5:
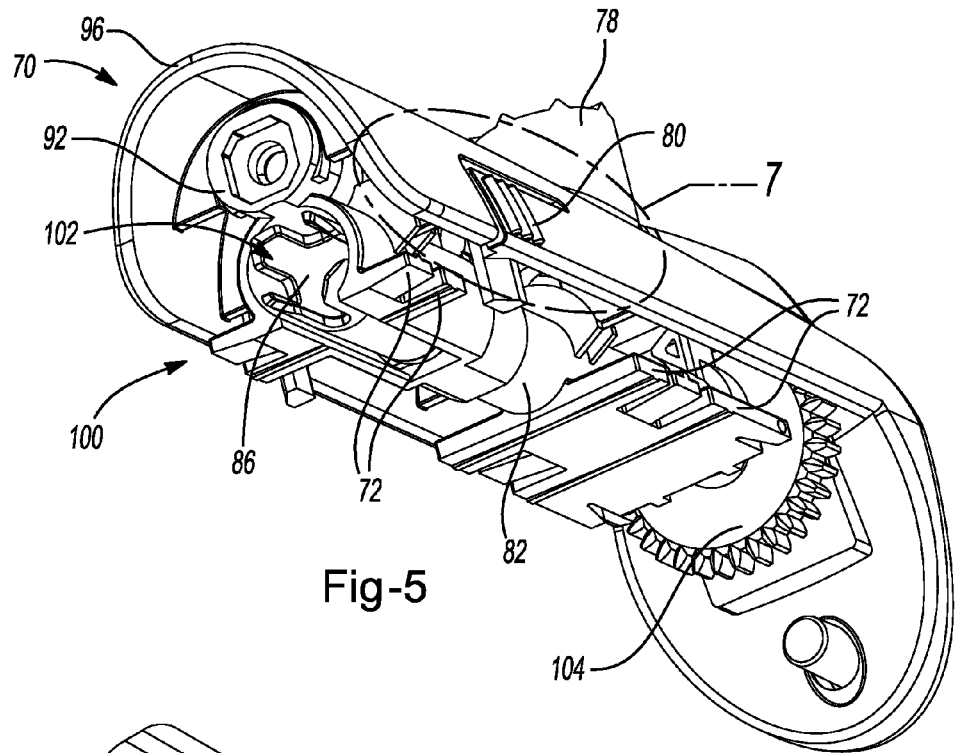
FIG. 5 illustrates a front perspective view of one example of a tubeset.

FIG. 5 illustrates a front perspective view of one possible configuration of a tubeset 70 as taught herein. The tubeset 70 includes a cover 96 that extends over the drivetrain 100 and the other components of the tubeset 70. The tubeset 70 includes a coupler 102 in a front region of the tubeset 70. The coupler 102 forms part of a suction port 86 that connects to a suction bridge so that a suction line 84 (not shown) may remove material. The rear region of the tubeset 70 includes a power transfer device 104 that is connected to and rotates the suction bridge 82. A fluid port 92 is located above the coupler 102 and the suction bridge 82. The cover 96 includes locking tabs 80 that lock the tubeset 70 to the handpiece 40 (not shown). An image guidance port 78 is formed in the cover 96 so that an image guidance system (not shown) may be attached. The drivetrain 100 includes rails 72 for attaching the tubeset 70 to the handpiece 40 (not shown).

Figure 6:
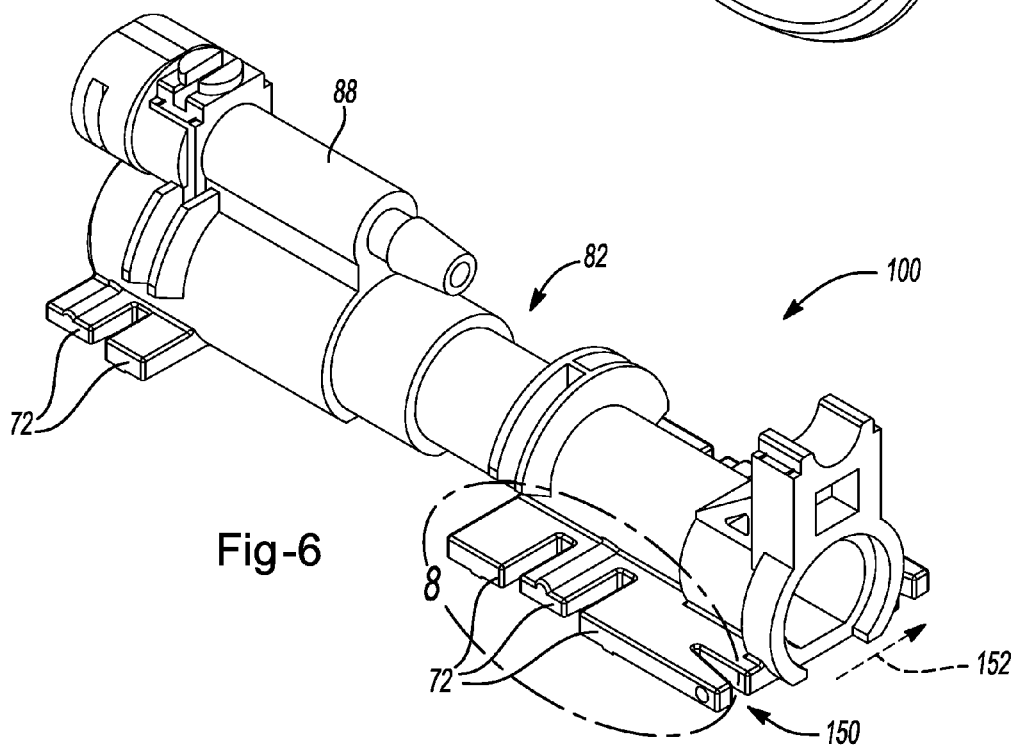
FIG. 6 illustrates a perspective view of one example of a drivetrain with a cover removed.

FIG. 6 illustrates a drivetrain 100 with the cover 96 removed. The coupler 102 is connected to the suction bridge 82 that extends the length of the drivetrain 100. A fluid bridge 88 is connected to the top of the suction bridge 82. The bottom side of the suction bridge 82 is connected to a plurality of rails 72 for attaching and aligning the drivetrain 100 to the handpiece 40 (not shown). As illustrated, the last rail includes a cutout 150 that allows the rail (left rail as illustrated) to deflect in the direction 152 (a corresponding right rail would deflect in a direction opposite to that of direction 152) during installation as is illustrated in more detail in FIG. 8.

Figure 7:
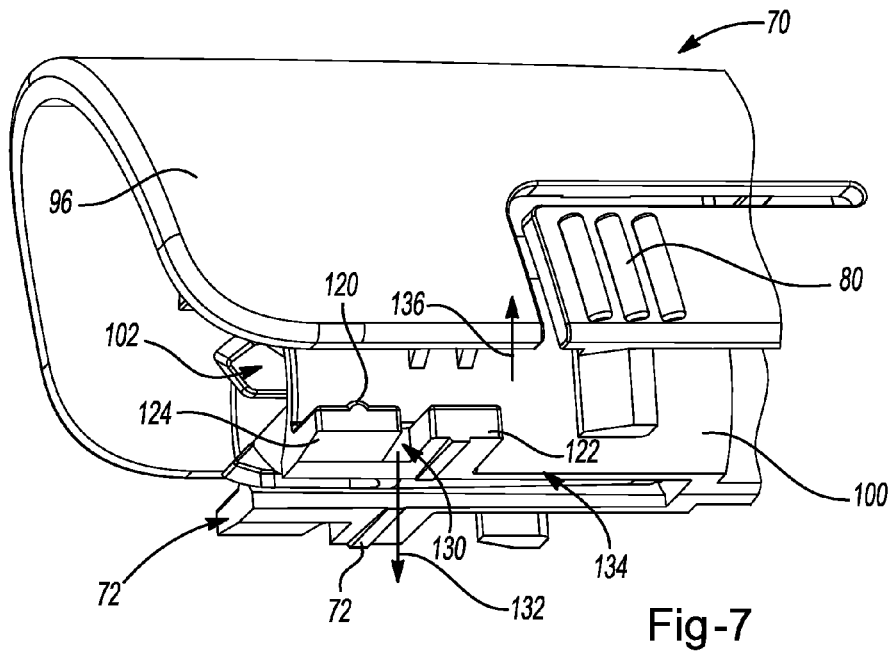
FIG. 7 illustrates a side view of the rear rails shown of the drivetrain in FIG. 6.

FIG. 7 illustrates a forward region of the tubeset 70 of FIG. 5. The forward region includes a cover 96. The cover 96 has locking tabs 80 that lock the tubeset 70 and drivetrain 100 to the handpiece 40 (not shown). The locking tabs 80 are depressible so that the tubeset 70 is lockable and removable, and so that the locking tabs 80 produce a force and assist in axially aligning the tubeset 70 during installation. The cover 96 is connected to and covers a drivetrain 100. The drivetrain 100 includes rails 72 that assist in installing the tubeset 70 in a handpiece 40 (not shown). A leading forward spring rail 130 includes a bump 120 and a relief 124 so that the forward spring rail 130 deflects in the direction 132 during installation. A trailing forward spring rail 134 includes a surface 122 so that the trailing forward spring rail 134 deflects in the direction 136 during installation.

Figure 8:
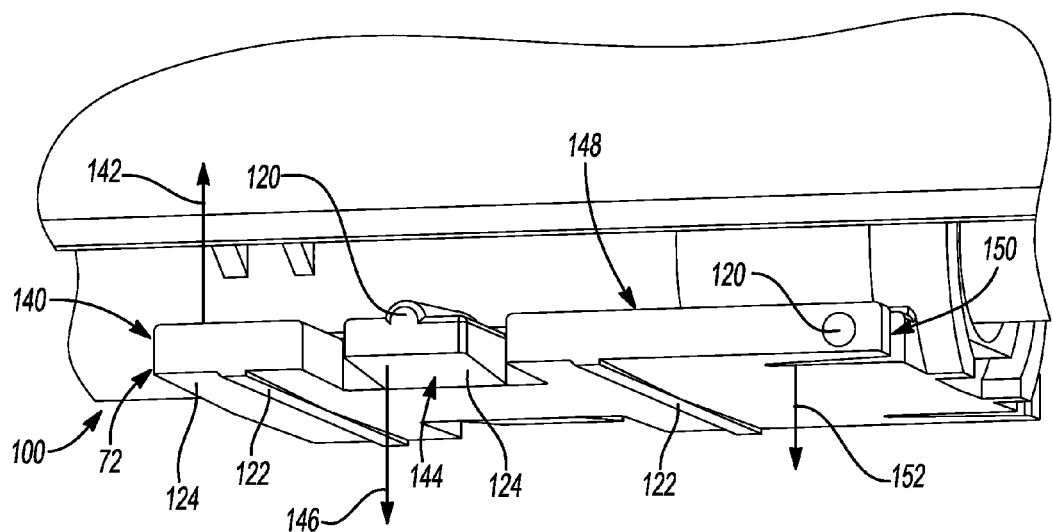
FIG. 8 illustrates a side view of the front rails shown in FIG. 5.

FIG. 8 illustrates a close-up view of the rails 72 located on the rear end the drivetrain 100 of FIG. 6. As illustrated, the rear end of the drivetrain includes three rails 72. Two of the rails include bumps 120 and two of the rails 72 include surfaces 122. The bumps 120 and surfaces 122 assist in maintaining the rails 72 within the tracks 44 (not shown) and once the rails 72 travel a desired distance the bumps 120 and surfaces 122 assist in preventing movement of the drivetrain 100. For example, the bumps 120 and surfaces 122 contact an adjacent surface of the handpiece 40 (not shown) so that alignment between the drivetrain 100 and the handpiece 40 (not shown) is maintained. Two of the rails 72 are vertical spring rails and include reliefs 124 and one of the rails is a horizontal spring rail. The reliefs 124 allow the rails 72 to move, due to the bumps 120 and/or the surfaces 122 contacting an adjacent surface, without the relief 124 portion contacting a corresponding portion of the handpiece 40 (not shown). For example, in FIG. 8 the leading rear spring rail 140 and the central rear spring rail 144 include reliefs 124. The leading rear spring rail 140 includes a relief 124 and a surface 122 on the bottom side so that during installation only the surface 122 contacts a track 44 (not shown) and the surface moves the leading rear spring rail 140 in a direction 142. The central rear spring rail 144 includes a relief 124 on a bottom side and a bump 120 on a top side so that the central rear spring rail 144 is moved in a direction 146. As the bump 120 contacts a track 44 (not shown) during installation the bump 120 moves the central rear spring rail 144 and the relief 124 prevents the bottom surface from contacting the track 44 (not shown) which results in both improved alignment due to the spring force of the central rear spring rail 144 maintaining the position of the drivetrain 100 and reduced friction due to the bump 120 being the primary contact surface during installation so that the surface area being contacted is reduced. The trailing rear spring rail 148 includes a bump 120 on a vertical side and a cutout 150 so that when the bump 120 contacts an adjacent surface the trailing rear spring rail 148 moves in the direction 152 due to the open space created by the cutout 150. During installation the spring rails enter the handpiece 40 (not shown) so that the leading rear spring rail 140 enters first, then the central rear spring rail 144, and finally the trailing rear spring rail 148.

Figure 9:
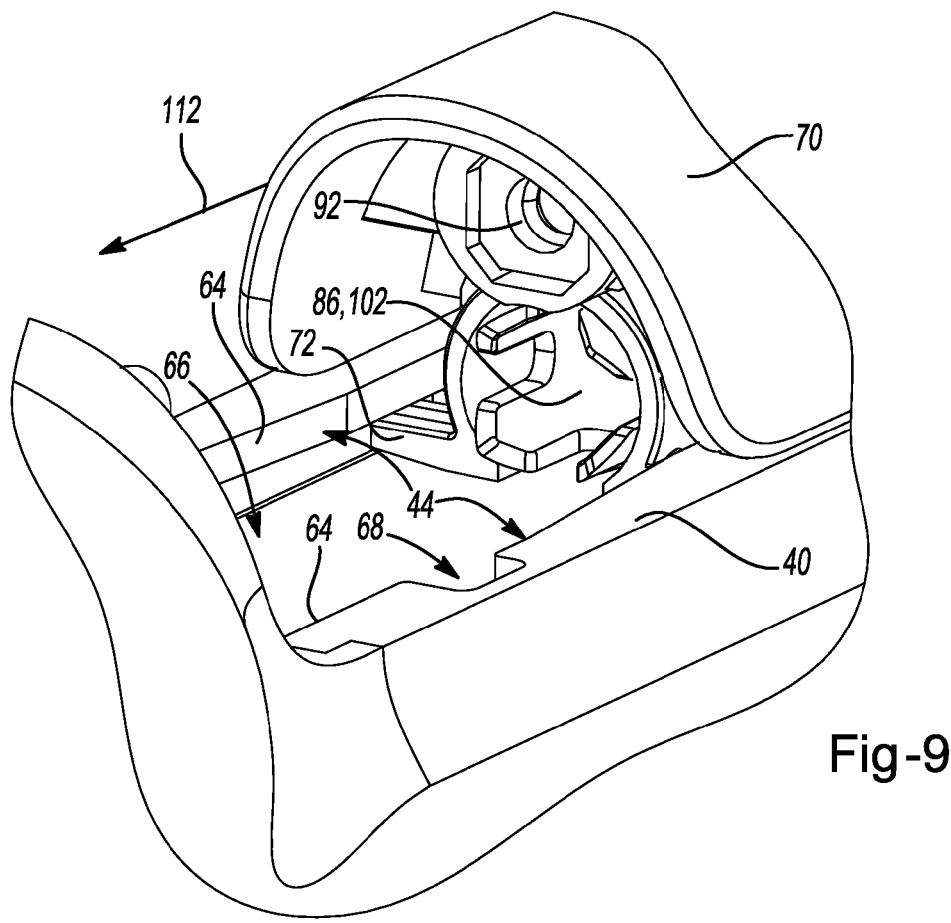
FIG. 9 illustrates a front perspective view of the tubeset attaching to the handpiece shown in FIG. 1.

FIG. 9 illustrates a close-up front view of FIG. 1, with the tubeset 70 being installed onto the handpiece 40 in the direction of attachment 112. The handpiece 40 includes tracks 44 that run the length of the handpiece 40. The tracks 44 have an upper surface 64 that overhangs the handpiece 40 so that a gap 66 is created under the upper surface 64. As illustrated the rails 72 of the drivetrain 100 fit under the upper surface 64 and slide along the gap 66 until the tubeset 70 is connected to the handpiece 40. The gap 66 decreases in size as the gap extends form a rear region 62 (not shown) to a front region 58 (not shown) of the handpiece 40 so that a friction fit is formed between the tracks 44 and the rails 72 and so that the handpiece 40 and the tubeset 70 are properly aligned. The handpiece 40 includes a recess 68 that corresponds to the locking tabs 80 (not shown) of the tubeset 70 so that the locking tabs 80 (not shown) removably lock the tubeset 70 to the handpiece 40. The tubeset 70 is moved in the direction 112 until the fluid port 92, the suction port 86, and the coupler 102 connect to the interchangeable tip 10 (not shown).

Figure 10:
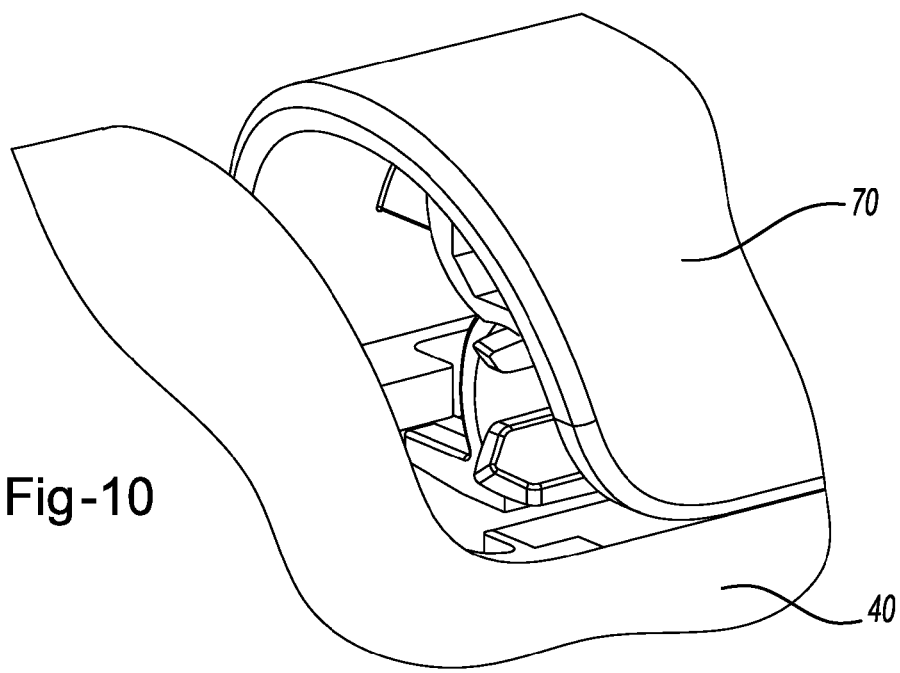
FIG. 10 illustrates a front perspective view of the tubeset almost completely attached to the handpiece.

FIG. 10 illustrates the tubeset 70 almost installed on the handpiece 40.

Figure 11:
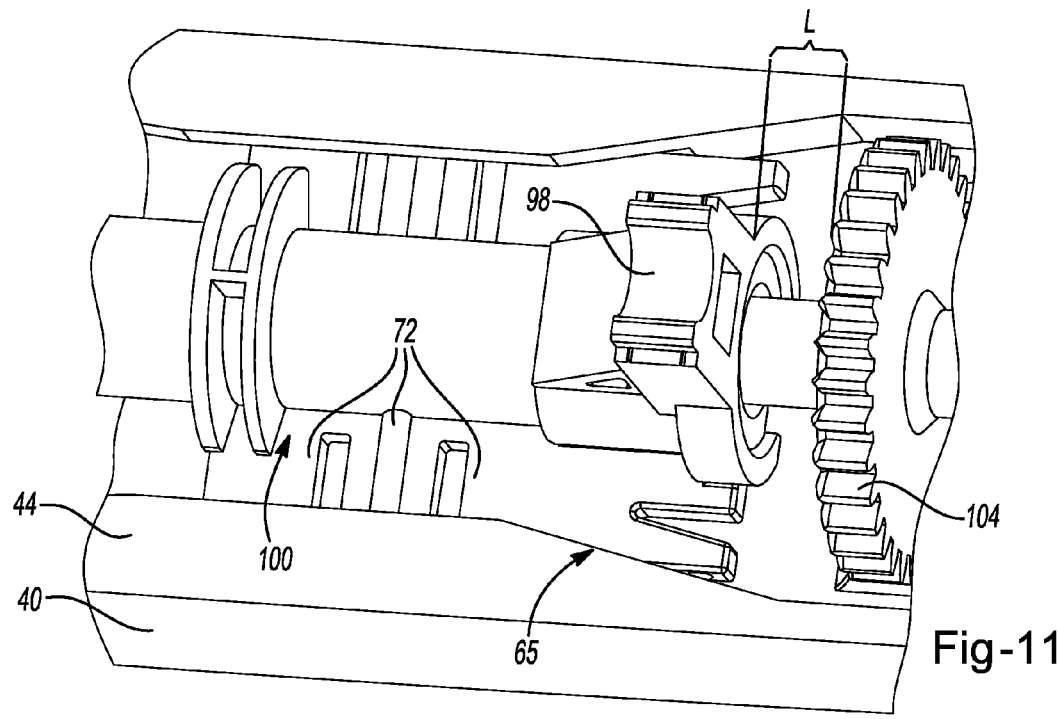
FIG. 11 illustrates a drivetrain without a cover connected to a handpiece.

FIG. 11 illustrates the drivetrain 100 partially installed in the handpiece 40 and the cover 96 removed. The track 44 includes a leading portion 65 that assists the drivetrain 100 in entering the handpiece 40 during the initial stages of installation. When the drivetrain 100 is fully installed the power transfer device 104 extends out from the drivetrain 100 a distance (L) so that the power transfer device 104 connects to the motor 46 (not shown). The drivetrain 100 includes a fluid line support 98 so that a fluid line 90 (not shown) extends over the rear of the drivetrain and connects to the fluid bridge 88 (not shown). The interference fit between the tracks 44 and the rails 72 are demonstrated so that the drivetrain 100 is aligned in the handpiece 40.

Figure 12:
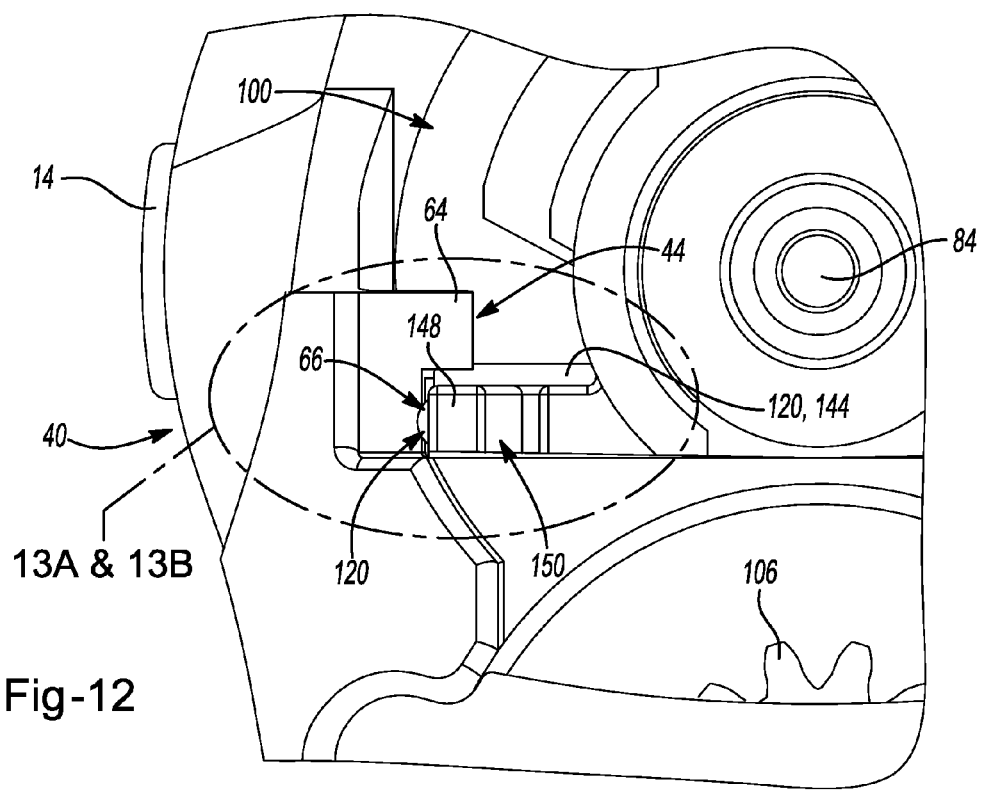
FIG. 12 illustrates a rear view of a drivetrain connected to a hand piece with the power transfer device removed.

FIG. 12 illustrates the drivetrain 100 with the cover 96, the handpiece cap 41, and the power transfer device 104 removed, and the drivertrain 100 fully inserted in the handpiece 40. The interference fit between the trailing rear spring rail 148 is shown as the trailing rear spring rail 148 extends into a gap 66 of the track 44. As illustrated, a bump 120 on a central rear spring rail 144 is in contact with the upper surface 64 so that the central rear spring rail 144 assists in alignment during installation. The bump 120 on the outside of the trailing rear spring rail 148 is in contact with the track 44 so that the cutout 150 is compressed and an interference fit is achieved. The motor power transfer device 106 is illustrated extending above the handpiece 40, and the motor drive power transfer device 106 is illustrated as being located below a suction line 84. The connecting tabs 14 of the interchangeable tip 10 (not shown) are illustrated extending through the handpiece 40 so that the interchangeable tip is connected to the handpiece 40.

Figure 13A:
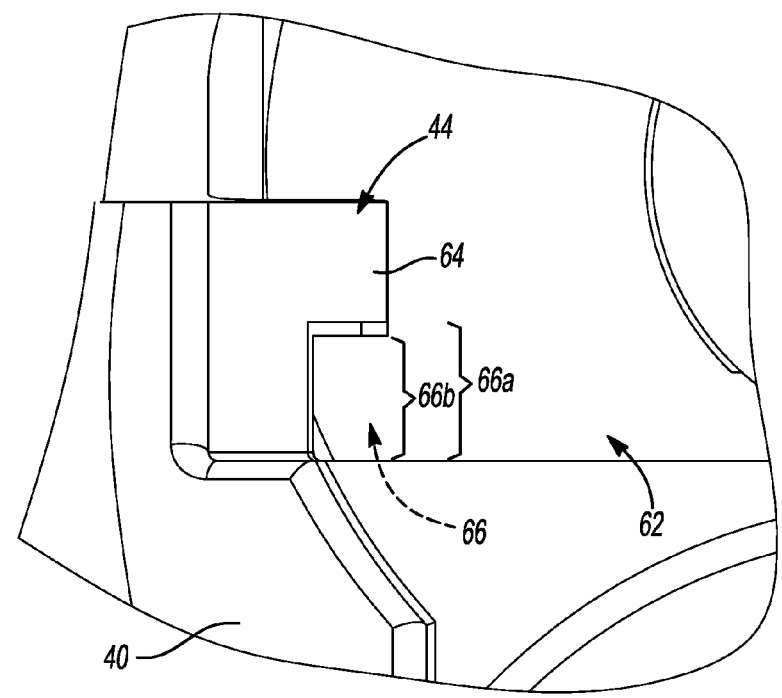
FIGS. 13A and 13B illustrate a close-up views of possible connection regions in a front region.

FIG. 13A is a close-up view when viewed from a rear region 62 of the handpiece 40 of FIG. 12 with the tubeset 70 removed. The upper surface 64 of the track 44 is shown overhanging the handpiece 40. The upper surface has a gap 66 that is formed between the bottom of the upper surface 64 and the top of the handpiece 40. The size of the gap 66 varies as the track 44 extends from a rear region to a front region. As illustrated, the size of the gap 66 in the rear region is indicated by length 66A and the size of the gap in the front region is indicated by length 66B. The size of the gap 66 is smaller in the front region so that the gap assists the tubeset (not shown) in aligning when the tubeset is installed in the handpiece 40.

Figure 13B:
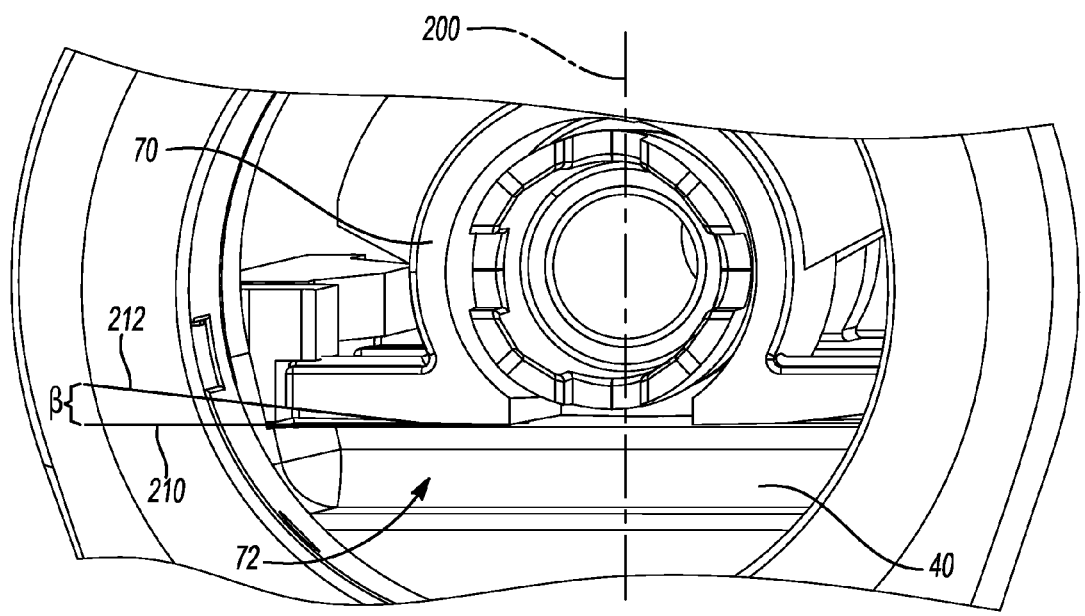

FIG. 13B is a close-up view of another configuration of the tubeset 70 connected to the handpiece 40 when the tubeset 40 is fully inserted. A central portion of the rails 72, along a centerline 200, forms a plane 210 and the rails 72 angle upward along a plane 212 as they extend outward from the central portion and form an angle (β) between plane 212 and plane 210.

Figure 14:
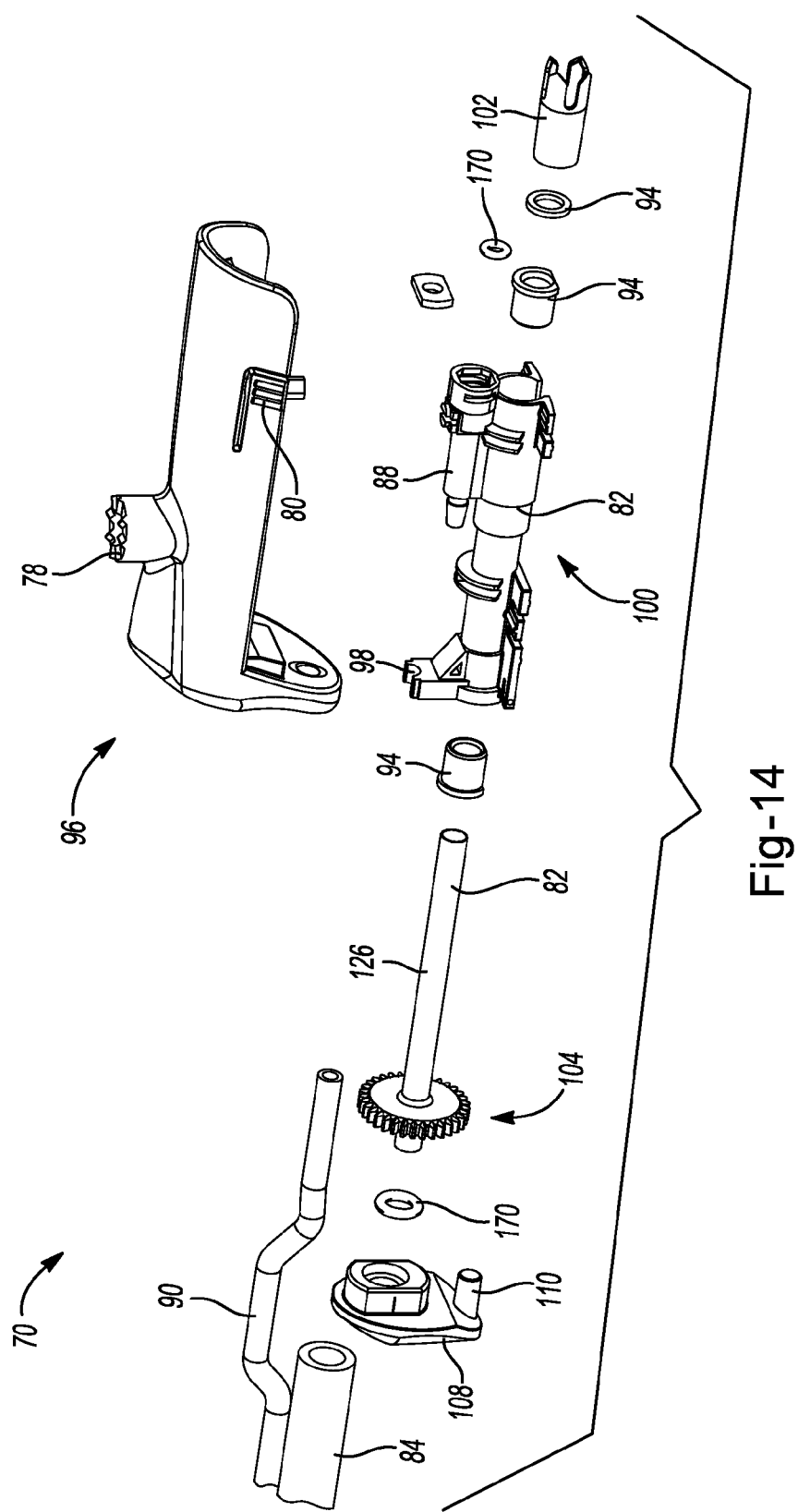
FIG. 14 illustrates an exploded view of one example of a tubeset taught herein.

FIG. 14 illustrates an exploded view of a tubeset 70. The tubeset has a cover 96 that includes an image guidance port 78 and locking tabs 80 on each side of the cover 96. The cover 96 includes a rear plate 108 that has a rear plate alignment projection 110 that assists in aligning the tubeset 70 with a handpiece 40. A suction line 84 and a fluid line 90 extend into and through the cover 96 and into contact with the suction bridge 82 and the fluid bridge 88 respectively. The fluid line 90 contacts a fluid line support 98 and then connects to the fluid bridge 88. The suction line 84 extends through the rear plate 108 and connects to the drive shaft 126, which extends through the drivetrain 100, and also serves as part of the suction bridge 82. The drive shaft 126 includes a power transfer device 104 and a plurality of bearings 94 so that the drive shaft 126 and coupler 102 are rotated by the power transfer device 104 during use. As illustrated, seals 170 are located in connection regions between the suction line 84 and the drive shaft 126 and the fluid line 90 and the fluid bridge 88.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A device comprising:
   a. a handpiece having one or more attachment ports and one or more tracks;
   b. a tubeset having:
      i. one or more attachment features for connecting the tubeset to the one or more attachment ports in the handpiece;
      ii. a drivetrain;
   c. a removable tip having an attachment arm for attaching to the one or more attachment ports in the handpiece;
   wherein the handpiece includes an attachment port that attaches the handpiece to an active lead and a return lead and the device is adapted to use only the active lead or both leads so that the device can switch between bi-polar energy and mono-polar energy;
   wherein the drivetrain includes a coupler that attaches the drivetrain to the removable tip so that the drivetrain moves at least a portion of the removable tip;
   wherein the tubeset, the hand piece, the drivetrain, one or more power transfer devices, or a combination thereof are made of plastic, and
   wherein the coupler is hollow so that items may be moved through the coupler while the coupler is attached to the removable tip.

2. The device of claim 1, wherein one of the one or more attachment features for connecting the tubeset is a rail and the tubeset includes one or more rails.

3. The device of claim 2, wherein the one or more tracks correspond to the one or more rails of the tubeset so that the one or more tracks and the one or more rails form a fixed connection.

4. The device of claim 2, wherein the one or more rails include a bump, a surface, a relief, or a combination thereof that assists in aligning the tubeset and the handpiece.

5. The device of claim 2, wherein at least one of the one or more rails includes a cutout so that when the at least one of the one or more rails contacts a part of the handpiece, the at least one of the one or more rails is compressible via the cutout.

6. The device of claim 3, wherein the one or more tracks include an upper surface that overhangs at least a portion of the handpiece so that the overhang forms a gap.

7. The device of claim 1, wherein the coupler is fixedly attached to one or more power transfer devices, and the coupler is axially mounted so that the coupler moves around an axis of rotation of one of the one or more power transfer devices so that the one of the one or more power transfer devices aligns with a power transfer device of the handpiece.

8. The device of claim 3 wherein at least one of the one or more attachment features is a spring rail so that during installation the spring rail is deflected by the one or more tracks so that the spring rail and the one or more tracks forms an interference fit.

9. The device of claim 1, wherein the tubeset includes one or more locking tabs that lock the tubeset to the hand piece.

10. The device of claim 1, wherein the drivetrain includes a fluid bridge that connects to a tube of the tubeset so that fluid is conducted through the drivetrain.

11. The device of claim 10, wherein the handpiece includes a motor power transfer device that is in communication with a power transfer device of the tubeset when the tubeset is connected to the hand piece.

12. A method comprising:
   a. obtaining each individual part of the device of claim 1;
   b. connecting a power source to the handpiece via a first attachment port of the one or more attachment ports;
   c. connecting the removable tip to the handpiece via a second attachment port of the one or more attachment ports; and
   d. connecting the tubeset to the handpiece via a third attachment port of the one or more attachment ports; and
      wherein the step of connecting the tubeset includes aligning the one or more rails of the tubeset with the one or more tracks of the handpiece so that the one or more tracks guide the tubeset into alignment with the removable tip, the handpiece, or both; and
      wherein the step of connecting the removable tip to the handpiece via a second attachment port includes aligning the removable tip with the coupler in the drivetrain so that during operation the drivetrain moves the removable tip.

13. A device comprising:
   a. a handpiece having one or more attachment ports;
   b. a tubeset having one or more attachment features for connecting the tubeset to the one or more attachment ports in a proximal end of the handpiece;
   c. a removable tip having an attachment arm for attaching to the one or more attachment ports in the handpiece;
      wherein the device comprises one or more of the following:
         a) the handpiece includes an attachment port that attaches the handpiece to an active lead and a return lead and the device is adapted to use only the active lead or both leads so that the device can switch between bi-polar energy and mono-polar energy; and b) the handpiece connects to one or more electrical input lines and the removable tip is free of direct connection to the one or more electrical input lines;
   wherein the tubeset includes a drivetrain, and the drivetrain includes a coupler that attaches the drivetrain to the removable tip so that the drivetrain moves at least a portion of the removable tip;
   wherein the tubeset, the hand piece, the drivetrain, one or more power transfer devices, or a combination thereof are made of plastic, and
   wherein the coupler is hollow so that items may be moved through the coupler while the coupler is attached to the removable tip.

14. The device of claim 13, wherein one of the one or more attachment features for connecting the tubeset is a rail and the tubeset includes one or more rails.

15. The device of claim 14, wherein the handpiece includes one or more tracks and the one or more tracks correspond to the one or more rails of the tubeset so that the one or more tracks and the one or more rails form a fixed connection.

16. The device of claim 15, wherein at least one of the one or more rails is a spring rail so that during installation the spring rail is deflected by the one or more tracks so that the spring rail and the one or more tracks form an interference fit.

17. The device of claim 14, wherein the one or more rails include a bump, a surface, a relief, or a combination thereof that assists in aligning the tubeset and the handpiece.

18. The device of claim 14, wherein the one or more rails is at least two rails and one of the rails includes a bump on a horizontal surface and at least one of the rails includes a bump on a vertical surface.

19. The device of claim 13, wherein the tubeset includes one or more locking tabs that lock the tubeset to the hand piece.

20. The device of claim 13, wherein the drivertrain includes a fluid bridge that connects to a tube of the tubeset so that fluid is conducted through the drivetrain.

* * * * *